(12) United States Patent
Hassenpflug et al.

(10) Patent No.: US 10,874,818 B2
(45) Date of Patent: Dec. 29, 2020

(54) AEROSOL DELIVERY SYSTEM

(71) Applicant: Philip Morris USA Inc., Richmond, VA (US)

(72) Inventors: Eric Hassenpflug, Westerville, OH (US); Larry Keith Hooks, Jr., Columbus, OH (US); James A. Prescott, Columbus, OH (US); Ludwin Mora, Columbus, OH (US); Michael Scott Ulrich, Columbus, OH (US); Jane O'Loughlin, Galloway, OH (US); Steve Wilder, Blacklick, OH (US); William G. Atterbury, Columbus, OH (US); Thomas D. Haubert, Columbus, OH (US); Ryan Somogye, Grove City, OH (US); Michael Ko, Brookline, MA (US); Stephen C. Schmitt, Dublin, OH (US); Michael Lorenz, Gahanna, OH (US); Lawrence A. Weinstein, Warminster, PA (US); James Leamon, Warminster, PA (US)

(73) Assignee: Philip Morris USA Inc., Richmond, VA (US)

( * ) Notice: Subject to any disclaimer, the term of this patent is extended or adjusted under 35 U.S.C. 154(b) by 392 days.

(21) Appl. No.: 15/854,331

(22) Filed: Dec. 26, 2017

(65) Prior Publication Data
US 2018/0185604 A1 Jul. 5, 2018

Related U.S. Application Data

(60) Provisional application No. 62/440,273, filed on Dec. 29, 2016.

(51) Int. Cl.
*A61M 16/10* (2006.01)
*A61M 16/14* (2006.01)
(Continued)

(52) U.S. Cl.
CPC ........ *A61M 16/109* (2014.02); *A61M 11/007* (2014.02); *A61M 11/042* (2014.02);
(Continued)

(58) Field of Classification Search
CPC .. A61M 16/109; A61M 16/147; A61M 16/14; A61M 16/0054; A61M 11/042;
(Continued)

(56) References Cited

U.S. PATENT DOCUMENTS

| 4,089,176 | A | * | 5/1978 | Ashe | ................. | H05B 6/108 |
| | | | | | | 60/650 |
| 5,743,251 | A | | 4/1998 | Howell et al. | | |

(Continued)

FOREIGN PATENT DOCUMENTS

| GB | 2504732 A | 2/2014 |
| WO | 2015177044 A1 | 11/2015 |
| WO | 2015177253 A1 | 11/2015 |

OTHER PUBLICATIONS

International Preliminary Report on Patentability dated Jul. 11, 2019 in corresponding International Patent Application No. PCT/EP2017/084701, 10 pages.

(Continued)

*Primary Examiner* — Justine R Yu
*Assistant Examiner* — Mayisha M Khan
(74) *Attorney, Agent, or Firm* — Buchanan Ingersoll & Rooney PC

(57) ABSTRACT

An aerosol delivery system, which includes an aerosol delivery unit, the aerosol delivery unit including: a cartridge receiver, which is configured to receive a cartridge assembly; and an inductor configured to receive the cartridge assembly and heat a liquid formulation within a capillary tube to produce an aerosol by induction heating. The cartridge assembly including an active part of the cartridge (Continued)

assembly including a capillary tube; a susceptor, the susceptor configured to partially surround the capillary tube; and a pair of displaceable covers, which surround at least the capillary tube and the susceptor.

34 Claims, 32 Drawing Sheets

(51) Int. Cl.
   *A61M 11/00* (2006.01)
   *A61M 11/04* (2006.01)
   *A61M 16/00* (2006.01)
   *A61M 15/00* (2006.01)
   *A61M 16/08* (2006.01)

(52) U.S. Cl.
   CPC ........ *A61M 16/0054* (2013.01); *A61M 16/14* (2013.01); *A61M 16/147* (2014.02); *A61M 15/0003* (2014.02); *A61M 15/0066* (2014.02); *A61M 16/0816* (2013.01); *A61M 2205/127* (2013.01); *A61M 2205/14* (2013.01); *A61M 2205/273* (2013.01); *A61M 2205/3368* (2013.01); *A61M 2205/3606* (2013.01); *A61M 2205/368* (2013.01); *A61M 2205/3633* (2013.01); *A61M 2205/505* (2013.01); *A61M 2205/587* (2013.01); *A61M 2205/6018* (2013.01)

(58) Field of Classification Search
   CPC .......... A61M 11/007; A61M 2205/273; A61M 2205/3368; A61M 16/0816; A61M 2205/587; A61M 2205/3633; A61M 15/0066; A61M 2205/505; A61M 2205/6018; A61M 2205/14; A61M 2205/368; A61M 15/0003; A61M 2205/3606; A61M 2205/127; A61M 11/00; A61M 11/006; A61M 11/04–048; A61M 16/01; A61M 16/10; A61M 16/104; A61M 16/1075–109; A61M 16/18; A24F 47/008; A24F 40/10; A24F 40/40; A24F 40/49; A24F 40/42; A24F 40/00; H05B 3/42; H05B 3/141
   See application file for complete search history.

(56) References Cited

U.S. PATENT DOCUMENTS

| | | | |
|---|---|---|---|
| 8,251,055 B2 | 8/2012 | Srinivasan et al. | |
| 8,701,658 B2 | 8/2014 | Mazela et al. | |
| 9,352,114 B2 | 5/2016 | Mazela et al. | |
| 9,592,361 B2 | 3/2017 | Mazela et al. | |
| 9,713,687 B2 | 7/2017 | Leamon et al. | |
| 2002/0078956 A1 | 6/2002 | Shame et al. | |
| 2003/0108342 A1 | 6/2003 | Sherwood et al. | |
| 2004/0081624 A1 | 4/2004 | Nguyen et al. | |
| 2008/0021377 A1* | 1/2008 | Kienman | A61M 1/3434 604/29 |
| 2008/0022999 A1* | 1/2008 | Belcastro | A61M 11/041 128/200.14 |
| 2008/0110458 A1 | 5/2008 | Srinivasan et al. | |
| 2008/0319383 A1* | 12/2008 | Byland | A61M 5/1782 604/67 |
| 2009/0230117 A1* | 9/2009 | Fernando | H05B 3/20 219/490 |
| 2009/0267242 A1 | 10/2009 | Nichols et al. | |
| 2012/0330228 A1* | 12/2012 | Day | A61M 5/31525 604/82 |
| 2014/0130880 A1* | 5/2014 | Schon | A61M 16/01 137/10 |
| 2014/0174383 A1* | 6/2014 | Kesten | F22B 21/00 122/494 |
| 2014/0276550 A1* | 9/2014 | Uram | A61M 5/16877 604/503 |
| 2015/0223292 A1* | 8/2015 | Duffield | H05B 6/06 219/634 |
| 2015/0245669 A1 | 9/2015 | Cadieux et al. | |
| 2016/0256621 A1* | 9/2016 | Toro | A61M 5/008 |
| 2018/0027877 A1* | 2/2018 | Tucker | A24F 40/40 |

OTHER PUBLICATIONS

International Search Report and Written Opinion dated Jun. 14, 2018 in corresponding International Patent Application No. PCT/EP2017/084701, 18 pages.

Partial International Search Report dated Mar. 26, 2018 in corresponding International Patent Application No. PCT/EP2017/084701, 12 pages.

* cited by examiner

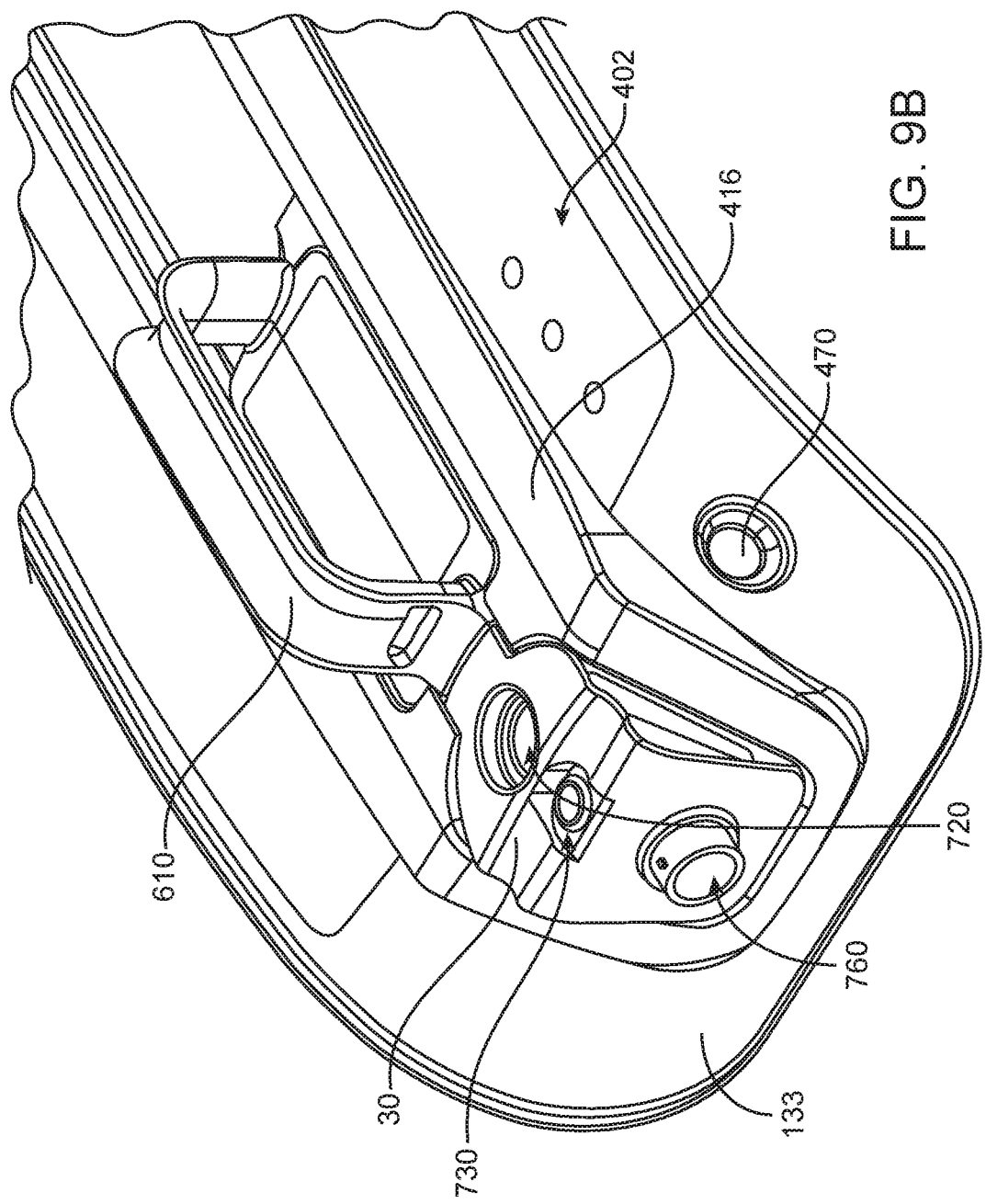

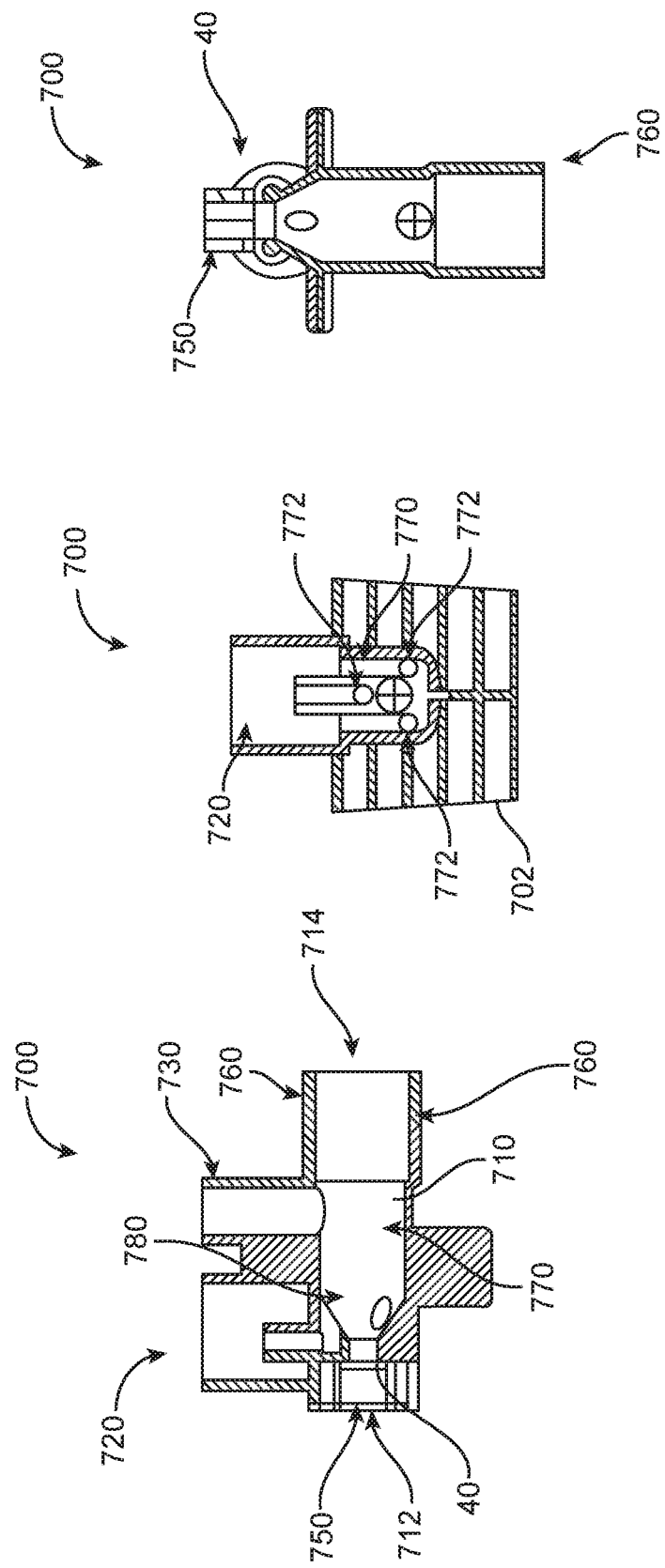

AEROSOL DELIVERY SYSTEM

CROSS-REFERENCE TO RELATED APPLICATION

This application claims priority under 35 U.S.C. § 119(e) to U.S. Provisional Application No. 62/440,273, filed on Dec. 29, 2016, the entire contents of which is incorporated by reference thereto.

STATEMENT UNDER 35 U.S.C. § 202(c)

Pursuant to 35 U.S.C. § 202(c), it is acknowledged that the United States Government may have rights in the invention described herein, which was made in part with funding from the National Heart, Lung, and Blood Institute (NHLBI) of the National Institutes of Health (NIH), Grant Nos. 4R44HL107000-02 and 2R44HL107000-03.

WORKING ENVIRONMENT

This disclosure relates to an aerosol delivery system for delivery of aerosol from an aerosol delivery unit, which is fed a liquid formulation from a syringe pump unit. The aerosol delivery system can also include a power control unit and operation interface. A carrier gas, such as a pressurized inspiratory gas, can be used to carry aerosol generated from the aerosol delivery unit to a patient.

Patients, both adult and infants, in respiratory failure or those with respiratory dysfunction are often mechanically ventilated in order to provide suitable rescue and prophylactic therapy. Mechanical ventilation can be invasive and non-invasive. Non-invasive ventilation can be provided to a patient capable of spontaneous breathing. A ventilatory circuit for administering non-invasive continuous positive airway pressure ventilation ("CPAP") includes a positive pressure generator connected by tubing to a patient interface, such as a mask, nasal prongs, or an endotracheal tube, and an exhalation path, such as tubing that allows discharge of the expired gases, for example, to the ventilator.

Producing medical aerosols with the use of a heated capillary generator have been disclosed in U.S. Pat. No. 8,251,055 and WO/2014/029827 A1. The ventilation gas tube, expiratory flow tube and entrained aerosol tube can be connected to the patient interface via an aerosol delivery connector, for example, as disclosed in WO 2009/117422 A2.

SUMMARY

A cartridge assembly is disclosed, the cartridge assembly comprising: an active part of the cartridge assembly including a capillary tube; a susceptor, the susceptor configured to partially surround the capillary tube; and a pair of displaceable covers, which surround at least the capillary tube and the susceptor.

An aerosol delivery system is disclosed, the aerosol delivery system comprising: an aerosol delivery unit, the aerosol delivery unit comprising: a cartridge receiver, which is configured to receive a cartridge assembly; and an inductor configured to receive the cartridge assembly and heat a liquid formulation within a capillary tube to produce an aerosol by induction heating.

A method is disclosed of producing an aerosol, the method comprising: placing a cartridge assembly into a cartridge receiver of an aerosol delivery unit, the cartridge assembly including (a) an active part of the cartridge assembly comprising (i) a capillary tube, (ii) a susceptor configured to at least partially surround the capillary tube, (iii) a handle, and (vi) an insulator, the handle and the insulator arranged on an upper surface of the susceptor, and (b) a pair of displaceable covers, which at least partially surround the insulator the capillary tube and the susceptor; and displacing the pair of displaceable covers by moving the active part of the cartridge assembly into an inductor.

BRIEF DESCRIPTION OF THE DRAWINGS

The disclosure is explained below with reference to the exemplary embodiments shown in the drawings. In the drawings:

FIG. 9B is a perspective view of a transition adaptor cover placed over the transition adaptor of the aerosol delivery unit in accordance with an exemplary embodiment.

FIG. 19 is a cross-sectional view of the transition adapter in accordance with an exemplary embodiment.

FIG. 20 is a cross-sectional view of the transition adapter in accordance with an exemplary embodiment.

FIG. 21 is a cross-sectional view of the transition adapter in accordance with an exemplary embodiment.

DETAILED DESCRIPTION

Aerosols are useful in drug delivery. For example, it is often desirable to treat respiratory ailments with, or deliver drugs by means of, aerosol sprays of fine, dispersed particles of liquid and/or solid, for example, pharmaceuticals, etc., which are inhaled and delivered into a patient's lungs. Aerosols can be generated by a heated capillary aerosol generator (CAG) by feeding a liquid formulation into a heated capillary tube or passage (referred to herein as "capillary", "heated capillary" or "heated capillary tube") while heating the capillary sufficiently such that the liquid formulation is at least partially volatilized, so that upon discharge from the heated capillary, the liquid formulation is in the form of an aerosol. The length of the capillary (or capillary tube) can depend on heat requirements dictated by, among other factors, the composition of the aerosol to be generated.

As used herein, the term "aerosol" refers to liquid or solid particles that are suspended in an air or gas. The "aerosol" or "aerosolized agent" referred to herein contains one or more of the active agents, as referred to below.

The term "ventilation" or "respiratory ventilation" as used herein refers to external mechanical or artificial support of a patient's breathing. The overall goals of mechanical ventilation are to optimize gas exchange, patient work of breathing and patient comfort while minimizing ventilator-induced lung injury. Mechanical ventilation can be delivered via positive-pressure breaths or negative-pressure breaths. Additionally, the positive-pressure breaths can be delivered noninvasively or invasively. Noninvasive mechanical ventilation (NIMV) generally refers to the use of a mask or nasal prongs to provide ventilatory support through a patient's nose and/or mouth. The most commonly used interfaces for noninvasive positive pressure ventilation are nasal prongs, nasopharyngeal tubes, masks, or nasal masks. NIMV can be distinguished from those invasive mechanical ventilatory techniques that bypass the patient's upper airway with an artificial airway (endotracheal tube, laryngeal mask airway or tracheostomy tube). NIMV can be provided by either bi-level pressure support (so called "BI-PAP") or continuous positive airway pressure (CPAP).

The employment of mechanical ventilation, whether invasive or non-invasive, involves the use of various respiratory gases, as would be appreciated by the skilled artisan. Respiratory gases are sometimes referred to herein as "CPAP gas," "ventilation gas," "ventilation air," "inspiratory flow," "expiratory flow," or simply "air." As used herein, the terms "ventilation gas", "air", "oxygen", "medicinal gas" and "gas" are used interchangeably to refer to a ventilation gas or flow driven oxygen/air and include any type of gas normally used for respiratory therapy. The term "ventilator" referred to herein can also be described as a source of ventilation gas. A carrier gas is used to carry aerosolized drugs in administering respiratory therapy. The term "carrier gas" can be used herein interchangeably with the term "entrainment gas" or "sheath gas" and includes any type of gas normally used for respiratory therapy as disclosed above.

A ventilation circuit for administering positive pressure ventilation includes a positive pressure generator or a source of positive end expiratory pressure (PEEP valve or column of water) connected by tubing to a patient interface, such as a mask, nasal prongs, or an endotracheal tube, and an exhalation path, such as tubing that allows discharge of the expired gases, for example, to the ventilator such as a constant flow CPAP or to an underwater receptacle as for "bubble" CPAP. The inspiratory and expiratory tubes can be connected to the patient interface via a "Y" connector or an aerosol delivery connector, for example, as disclosed in WO 2009/117422A2, which contains a port for attaching each of the inspiratory and expiratory tubes, as well as a port for the aerosol, the patient interface and, a port for attaching a pressure sensor.

The aerosol generated by the heated capillary or other means is known to be mixed with a carrier gas or sheath gas for transporting to the patient. Admixing the aerosol and sheath gas in a transition adapter is disclosed, for example, in U.S. Patent Publication Nos. 2008/0110458 and 2014/0053831, which are incorporated herein by reference in their entirety.

In an exemplary embodiment, the source of the carrier gas is a ventilator, which is used for providing ventilator support to the patient receiving aerosolized drug. In another embodiment, the source of the carrier gas is independent from a ventilator and is coming from a source of a positive flow. Preferably, the carrier gas is non-humidified. In accordance with an exemplary embodiment, the non-invasive breathing support can be provided to preterm infants with irregular breathing or lung diseases with continuous positive airway pressure (CPAP) given via nasal prongs or a mask. In accordance with an exemplary embodiment, it would be desirable to treat infants with an aerosol generated by an aerosol delivery system and carried by a carrier gas, such as a non-humidified gas to a patient.

Figure 1:
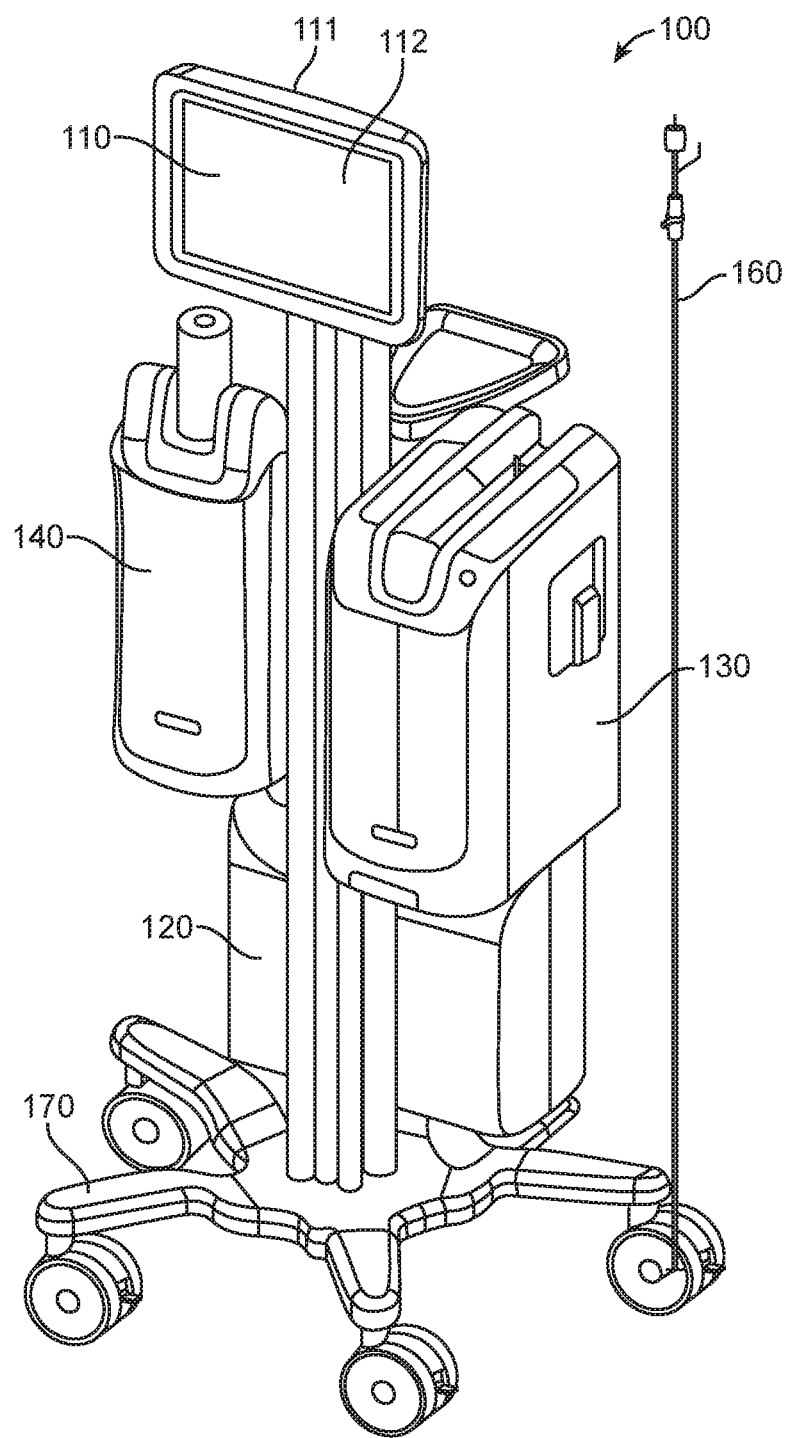
FIG. 1 is a perspective view of an aerosol delivery system in accordance with an exemplary embodiment.

FIG. 1 is a perspective view of an aerosol delivery system 100 in accordance with an exemplary embodiment. As shown in FIG. 1, the aerosol delivery system 100 can include an operator's interface unit (or touch screen interface) 110, a power control unit (or power controller) 120, an aerosol delivery unit 130, and a syringe pump unit (or syringe pump) 140. In addition, each unit 110, 120, 130, 140 can include a microprocessor or microcomputer having an operating system to carry out the processes as disclosed herein, The units 110, 120, 130, 140 are configured to be individually replaced and/or serviced, if necessary.

As shown in FIG. 1, for mobility, each of the units 110, 120, 130, 140, can be configured to be attachable to a wheeled pole or therapeutic cart 170. In addition, the system 100 can include a temperature probe 160. In accordance with an exemplary embodiment, a prominent light bar 111, for example, can be arranged at the top of the system 100, for example, on the touchscreen interface 110, and can communicate system status and can be visible, for example, if the operator is across the room and not looking directly at the display screen 110.

Figure 2:
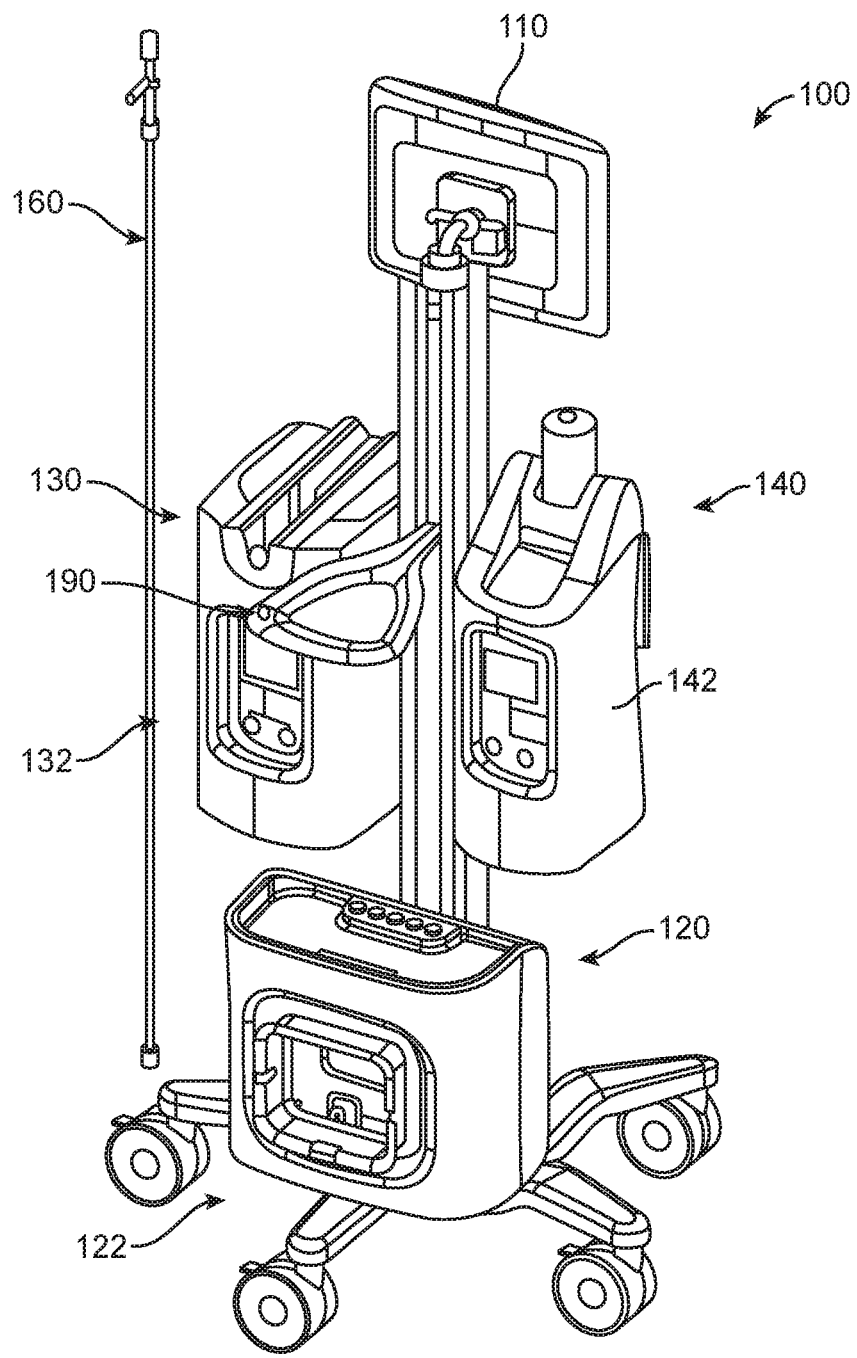
FIG. 2 is a perspective view of the aerosol delivery system as shown in FIG. 1 in accordance with an exemplary embodiment.

FIG. 2 is a perspective view of the aerosol delivery system 100 as shown in FIG. 1 in accordance with an exemplary embodiment. As shown in FIG. 2, operator's interface unit 110, the power control unit (or power controller) 120, the syringe pump unit 130, and the aerosol deliver unit 140, can have a separate or dedicated user interface, 112, 122, 132, 142, for preparing and operating each of the individual units 110, 120, 130, 140, and/or an entirety of the system 100. In accordance with an exemplary embodiment, each unit 110, 120, 130, 140 can have an operator's interface, such as, for example, an on/off button, touch screen, switch, latch, loading controls, which communicates with one or more of the other units 110, 120, 130, 140

Figure 3C:
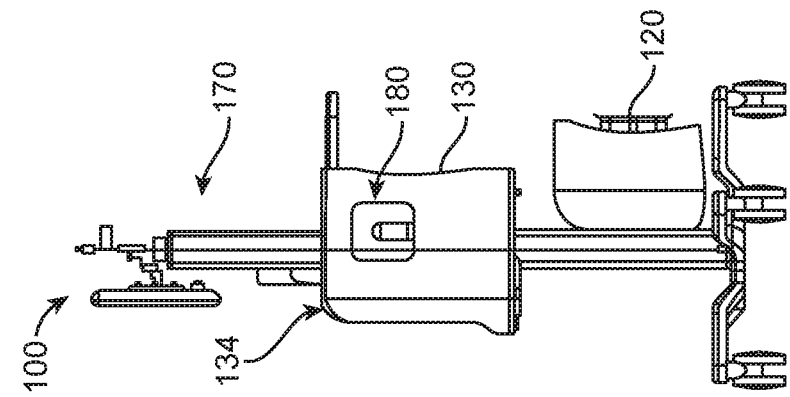
FIGS. 3A-3C are a side view, a front view, and another side view, respectively, of the aerosol delivery system as shown in FIG. 1 in accordance with an exemplary embodiment.
Figure 3B:
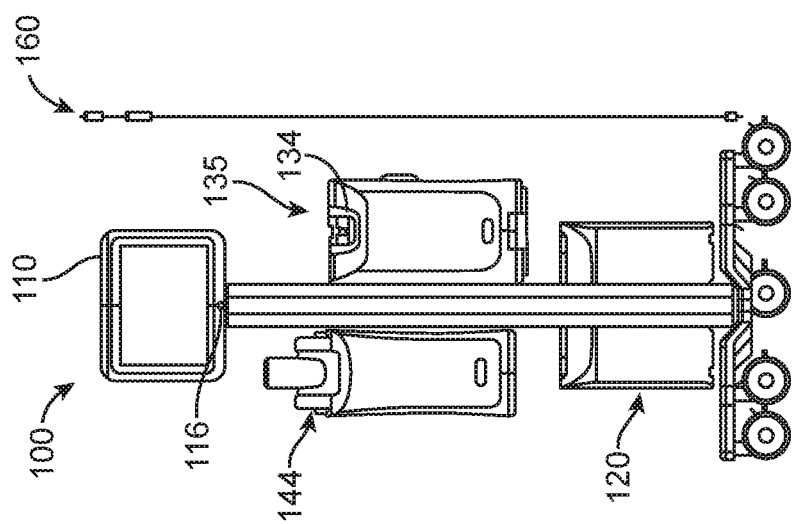
Figure 3A:
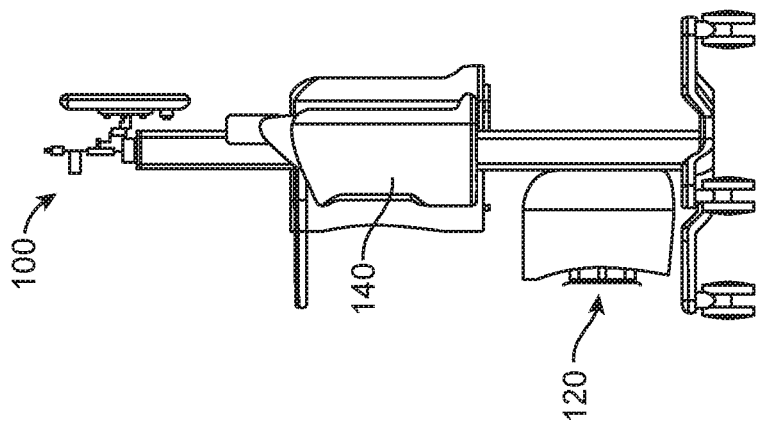

FIGS. 3A-3C is a side view, a front view, and another side view of the aerosol delivery system 100 as shown in FIG. 1 in accordance with an exemplary embodiment. In accordance with an exemplary embodiment, the working heights and positioning of the touchscreen interface or display unit 110, the syringe holder 144 of the syringe pump unit 140, the top cover of the cartridge receiver 134 and corresponding aerosol tubing connection area 135 of the aerosol delivery unit 130 can be optimized for the intended user's height and to facilitate administering treatment through the use of the therapeutic cart or wheeled pole 170.

In accordance with an exemplary embodiment, a prominent color highlights the primary user interface area on each unit 110, 120, 130, 140. For example, the body color of each unit 110, 120, 130, 140 can be predominantly white to show cleanliness and blend in with the surrounding environment. In accordance with an exemplary embodiment, on a side of the aerosol delivery unit 130, a hook feature (or cavity with a prong or hook) 180 can be incorporated for hanging/storing the aerosol tubing 800 (FIG. 22) and the temperature probe 160 when the system 100 is in storage and waiting for use. In accordance with an exemplary embodiment, wire/cable connectors (not shown) for each unit 110, 120, 130, 140 can be color-coded to facilitate proper connection during assembly. In accordance with an exemplary embodiment, the of the therapeutic cart or wheeled pole 170 can have a handle 190 to help assist an operator or user to move or change the location of the cart or wheeled pole 170 within a patient's room and/or the hospital.

In accordance with an exemplary embodiment, as shown in FIGS. 1-3C, the operator's interface unit (or display screen) 110 can be a touchscreen display system, which displays a treatment status to the operator and provides controls for operating the system through, for example, an interactive Graphical User Interface (GUI). The operator's interface unit 110 can also include an ON/OFF button or control 116 (FIG. 3B). In accordance with an exemplary embodiment, a light bar 111 can be arranged at the top of the system 100, for example, on the touchscreen interface 110, and can communicate system status and can be visible, for example, if the operator is across the room and not looking directly at the display screen 110.

Figure 4:
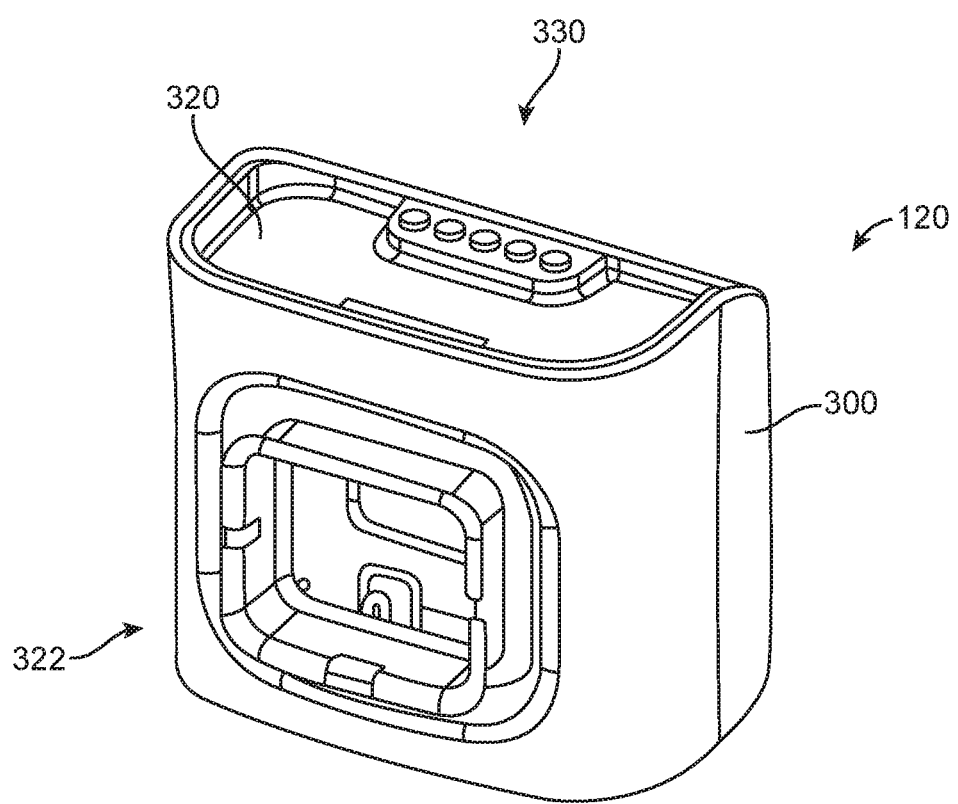
FIG. 4 is a perspective view of a power control unit of the aerosol delivery system in accordance with an exemplary embodiment.

FIG. 4 is a perspective view of a power control unit (or power controller) 120 of the aerosol delivery system 100 in accordance with an exemplary embodiment. The power control unit has a power input and a power output 322. As shown in FIG. 4, the power control unit 120 including a housing 300, which is arranged to house or provide, for example, one or more sources of power, for example, a 12V and/or a 48 V supply, a plurality of wire harnesses configured to supply power, for example, 12 VDC and/or 48 VDC, a power cord, a printed circuit board (PCB) panel, a display screen, an embedded computer or processor, and optionally, a fan. In accordance with an exemplary embodiment, the power control unit 120 can be plugged into an electrical source of power, or alternatively, the power control unit 120 can be battery powered or have an alternative source of power which powers the power supply in case an electrical source of power is not available.

In accordance with an exemplary embodiment, as shown in FIG. 4, the power control unit (or power controller) 120 can include a recess 320 on a top (or an upper surface) for storing extra disposable components and an integral cord wrap for storing and securing the power cord during storage. As shown in FIG. 4, on the top or upper surface of the housing 300 of the power control unit 120, a plurality of wire harnesses 330 are provided to connect the power control unit 120, for example, to the operator's interface unit 110 (FIG. 1), the aerosol delivery unit 130, and the syringe pump unit 140. The power control unit 120 can include an on/off switch, and a USB port for data exchange and software updates.

Figure 5:
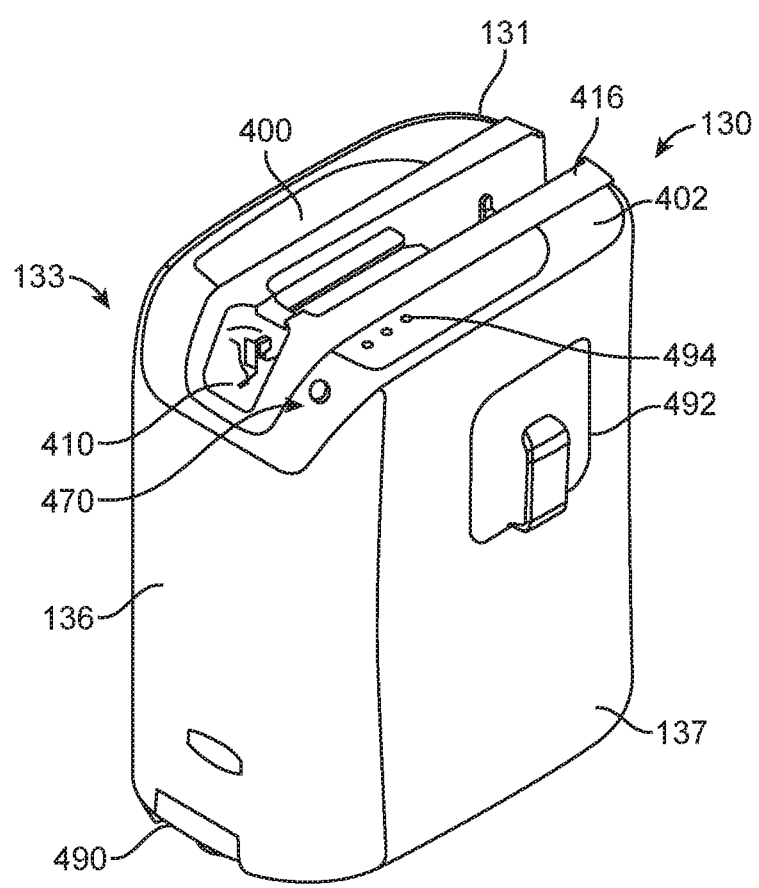
FIG. 5 is a perspective view of an aerosol delivery unit of the aerosol delivery system in accordance with an exemplary embodiment.

FIG. 5 is a perspective view of an aerosol delivery unit 130 of the aerosol delivery system 100 (FIG. 1) in accordance with an exemplary embodiment. As shown in FIG. 5, the aerosol delivery unit 130 includes a cartridge receiver 400 which is configured to receive (1) a cartridge assembly (or cartridge) 500 (FIG. 11 and FIG. 12), (2) a disposable aerosol tube set 800 (FIG. 22) which includes a transition adapter 700 (FIG. 9A and FIG. 9B), and (3) a temperature probe 160 (FIGS. 1-3C). In accordance with an exemplary embodiment, the cartridge assembly 500 is preferably a one-time use or disposable cartridge. The aerosol delivery unit 130 can have a connection 470 (FIG. 9A and FIG. 9B), for example, a temperature sensor jack for the temperature probe 160 on the top surface or cover 402. In addition, the aerosol delivery unit 130 can include a cup holder (or placement) 490 for a condensation trap (not shown) on a front panel 136, and tube storage 492 on a side panel 137. In an alternative embodiment, the temperature can be shown as a light bar or digital display, which can provide a signal to a user if the system 100 is working within a desired temperature range during use. Lights 494 on the top surface or cover 402 of the aerosol delivery unit 130 can provide feedback to the user regarding the unit's status. In accordance with an exemplary embodiment, a user makes the physical connection between (a distal end of the capillary 651 (FIG. 13) and a transition adapter 700 (FIG. 9A and FIG.

9B) on the cartridge receiver 400 by placing the active part of the cartridge 600 into a designated slot in the cartridge receiver 400.

Figure 6:
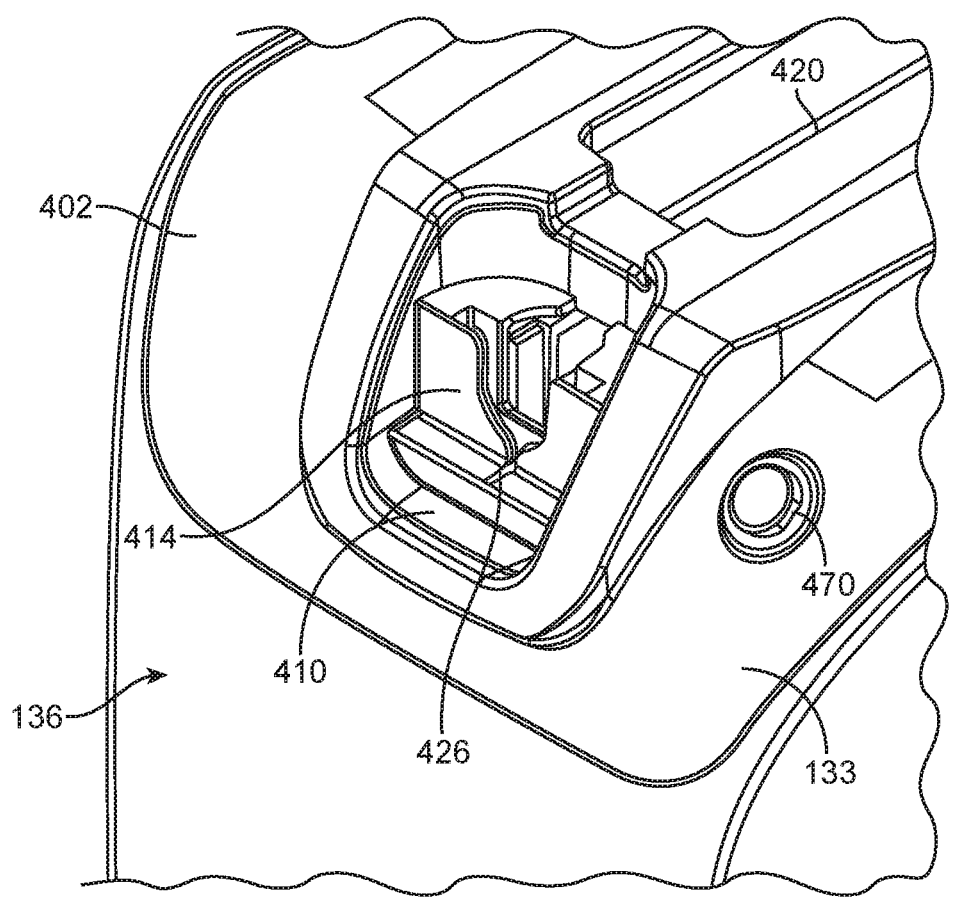
FIG. 6 is a perspective view of a portion of the aerosol delivery unit as shown in FIG. 5.
Figure 8A:
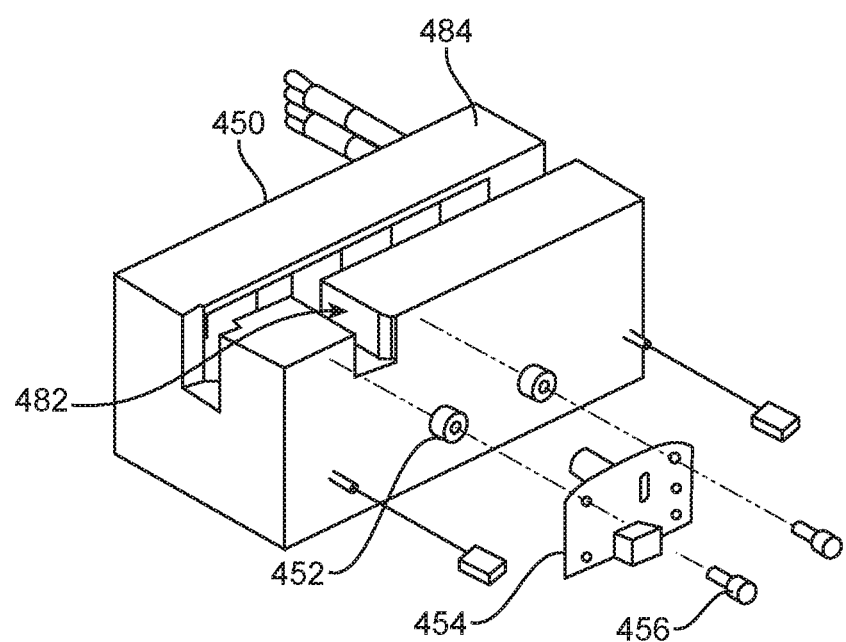
FIG. 8A is a perspective view of a potted inductor of the aerosol delivery unit in accordance with an exemplary embodiment.

FIG. 6 is a perspective view of the aerosol delivery unit 130 (FIG. 1) showing a portion of FIG. 5 on a distal end 133 of the cartridge receiver 400. As shown in FIG. 6, the distal end 133 of the aerosol delivery unit 130 includes an aerosol output pocket 410, an active alignment groove 420 configured to guide an active part of the disposable cartridge (or unshielded part of the cartridge) 600 into a potted inductor 450 (FIG. 8A), a transition adapter cavity 414, and a transition adapter placement groove 426, which connects with the transition adapter flag 704 (FIG. 18) such that when the flag 704 is inserted into the transition adapter placement groove 426, the light can be blocked, and a sensor 408A (FIG. 7A) signals that the transition adapter 700 has been placed in the cartridge receiver 400 (as shown, for example, in FIG. 9A).

FIG. 7A is an exploded perspective view of a portion of the aerosol delivery unit 130, a cartridge receiver 400 in accordance with an exemplary embodiment. As shown in FIG. 7A, the cartridge receiver 400 can include a top surface or cover 402 and a platform receiver 416. Alternatively, the cartridge receiver 400 can be made of a single part or more than two parts. The cartridge receiver 400 can include an optical sensor assembly (for example, an LED printed circuit board (PCB) assembly) 404 for displaying an operational status of the aerosol delivery unit 130, a first sensor PCB assembly 408A configured to sense the presence of the transition adapter 700 (FIG. 9A and FIG. 9B) on the distal end 133 (FIG. 9A and FIG. 9B) of the aerosol delivery unit 130 during use, and a second sensor PCB assembly 408B configured to detect the engagement of the capillary's tip with the transition adapter 700. A plurality of screws 406 can be used to attach the optical sensor assembly (or LED PCB assembly) 404 to the top cover 402. A plurality of screws 412 can be used to attach the first sensor PCB assembly 408A to the top cover 402. In addition, the top cover 402 can include a wire harness (including a connector) 409 for a temperature sensor 160 (FIG. 1). Hardware 438 can be used to attach the second sensor assembly 408B to the platform receiver 416.

In accordance with an exemplary embodiment, the cartridge receiver 400 can also include, near the proximal end 131 (FIG. 5) of the aerosol delivery unit 130, an item serving as a placement for the cartridge as the cartridge is first inserted into the cartridge receiver 400. As shown in FIG. 7A and FIG. 7B, a pair of placement pins 418 is configured to receive the cartridge 500 (FIG. 9A). The placement pins 418 can be attached to the platform receiver 416 by hardware 431. A cartridge identification (ID) PCB assembly 422 works together with a data card 670 (FIG. 12) to identify a cartridge 500 as new (or previously used) as well as to provide any other useful information and can be attached to the platform receiver 416 by hardware 424. A cartridge latch assembly 430 is configured to be actuated by a cartridge lock 458 (FIG. 8B) in the cartridge receiver 400. The cartridge latch assembly 430 can be attached to the platform receiver 416 by hardware 426, 428, 432, 434, and 436.

FIG. 7B is a perspective view of a pair of placement pins 418 in accordance with an exemplary embodiment. As shown in FIG. 7B and further described in detail below with reference to FIG. 9A and FIG. 9B, each of the placement pins 418 is configured to disengage the covers (to allow the active part of the cartridge 600 (FIG. 13) to move forward) once the disposable cartridge 500 is nested into the cartridge receiver 400 and keeps the covers 620, 630 in place and/or locked into the cartridge receiver 400 while the active part of the cartridge 600 is moved forward into the heating area (or inductor 450) and until the active part of the cartridge 600 is fully returned into the pair of covers 620, 630 (FIG. 11). As shown in FIG. 7B, each of the placement pins 418 has a generally cylindrical shape 440 with an inner cavity 442 having a relatively flat or planner surface 444 and a flange 446 on an upper end 448 of each pin 418. The inner cavity 442 of the placement pins is configured to allow the active part of the cartridge 600 freely move in and out of the covers.

FIG. 8A, FIG. 8B, and FIG. 8C are perspective views of another portion of the aerosol delivery unit 130 in accordance with an exemplary embodiment. As shown in FIG. 8A, the aerosol delivery unit 130 can include a heating unit such as a potted inductor 450. The inductor 450 includes an induction coil 462 (FIG. 8C) for heating the susceptor 660 (FIG. 13). The inductor 450 can be placed in the potted inductor holder 451 of the housing 460 (FIG. 8B) attached by screws or otherwise. As shown in FIG. 8A, the inductor 450 can include an assembly having an infrared (IR) sensor board 454 with an IR sensor 480 (see FIG. 10) placed in a groove 482 allowing the IR sensor 480 to sense the temperature of the susceptor 660. The IR sensor board 454 can be held in place and adjacent to the inductor 450 by hardware such as, for example, a pair of spacers 452 and a pair of bolts 456. The inductor 450 also includes a groove 484 configured to fit with the active alignment groove 420 (FIG. 7A) in the platform receiver and accommodate the susceptor 660.

As shown in FIG. 8B, the aerosol delivery unit 130 includes a housing 460 configured to receive the inductor 450. After the inductor 450 is fitted in the frame (or housing) 460 within the potted inductor holder 451 at the distal end 133 of the aerosol delivery unit, the groove 484 (FIG. 8A) is aligned with the active alignment groove 420 and the placement pins 418 in the platform receiver 416 (see FIG. 7A). The housing 460 also includes the cartridge lock 458, which locks the disposable cartridge 500 within cartridge receiver 400.

FIG. 8C is a perspective view of another portion of the aerosol delivery unit 130 in accordance with an exemplary embodiment. As shown in FIG. 8C, the potted inductor 450 is configured to be received in a distal portion (or front end) 463 of the housing 460. The inductor 450 includes an induction coil 462, which heats the susceptor 660 (FIG. 13). In accordance with an exemplary embodiment, the susceptor 660 is positioned inside of the inductor 450, which is composed of an induction coil 462, which can include a wire 461 wound around at least one graphite core 464, and more preferably wound around a plurality of graphite cores 464. The current in the wire 461 is modulated typical of an induction heating process by an inductor control unit (not shown), which is housed within the aerosol delivery unit 130. Most inductive heaters heat the susceptor 660 directly. However, in accordance with an exemplary embodiment, the graphite cores 464 of the inductor 450 couple the susceptor 660 to the inductor coil 462 instead.

FIG. 9A is a perspective view of a top portion of the aerosol delivery unit 130 with a cartridge 500 inserted into in the cartridge receiver 400 in accordance with an exemplary embodiment. As shown in FIG. 9A, the cartridge 500 can initially be placed onto the placement pins 418 (not shown) within the cartridge receiver 400 at a proximal end (or backside) 131 of the aerosol delivery unit 130 with a handle 610 remaining visible. This position of the cartridge 500 within the cartridge receiver 400 will be referred to as a starting position. The transition adapter 700 is placed at the distal end 133 (or front side) within the aerosol output pocket 410 and adjacent to the active alignment groove 420.

FIG. 9B shows the transition adaptor cover 30 placed over the transition adaptor 700. On the top cover 402, a temperature sensor jack 470 can be arranged, such that an operator or user can determine if the aerosol delivery unit 130 is operating within the working temperature range of, for example, from approximately, 150° C. to 300° C. Alternatively, rather than a temperature sensor jack 470, the jack can be replaced with a light or visual display, which can signal if the system 100 is working within the working temperature range.

Figure 9A:
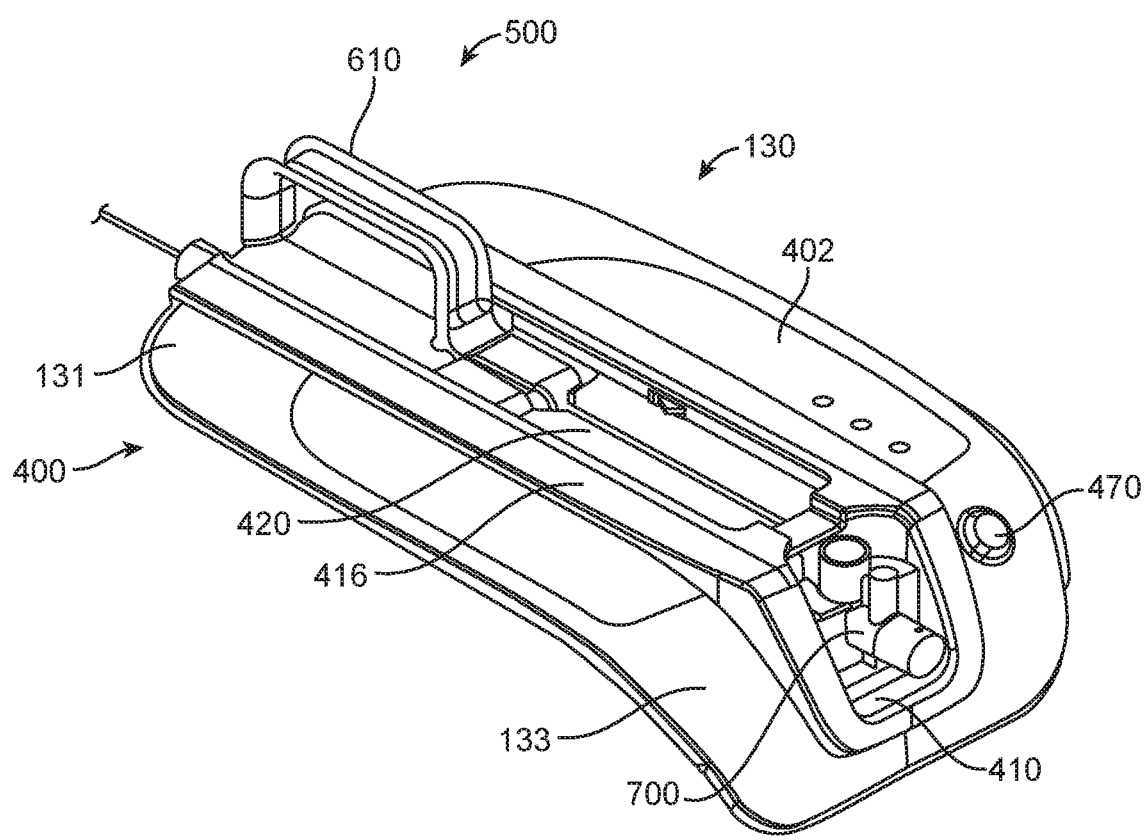
FIG. 9A is a perspective view of a disposable cartridge assembly in the user interface of the aerosol delivery unit in accordance with an exemplary embodiment.
Figure 15A:
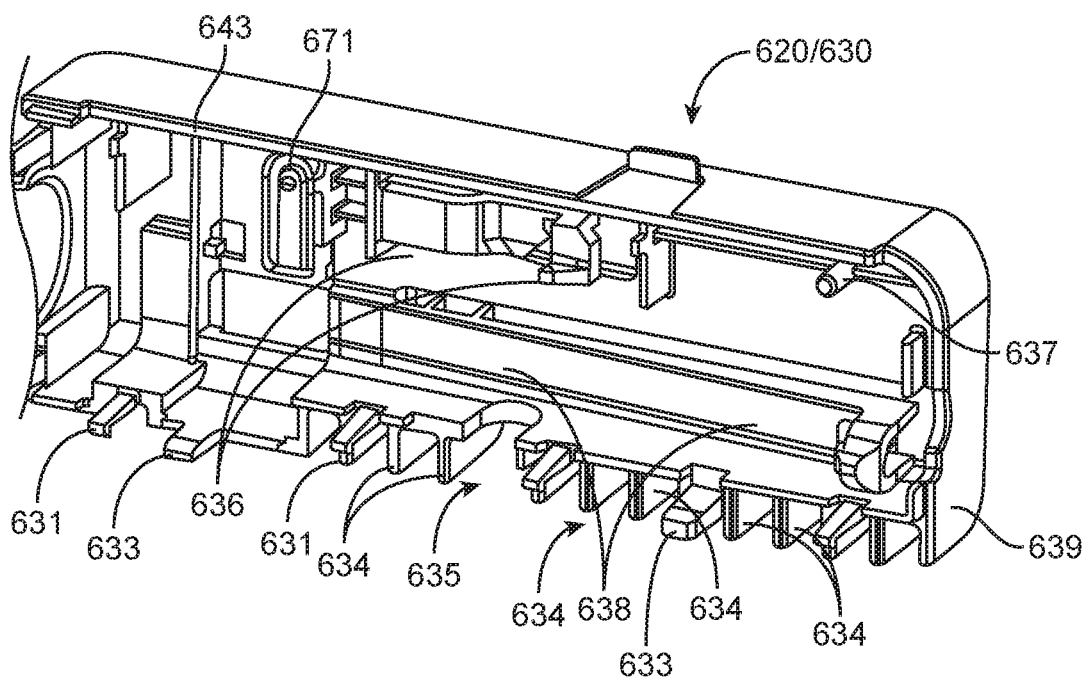
FIG. 15A is a perspective view of a cover of the disposable cartridge assembly in accordance with an exemplary embodiment.
Figure 15B:
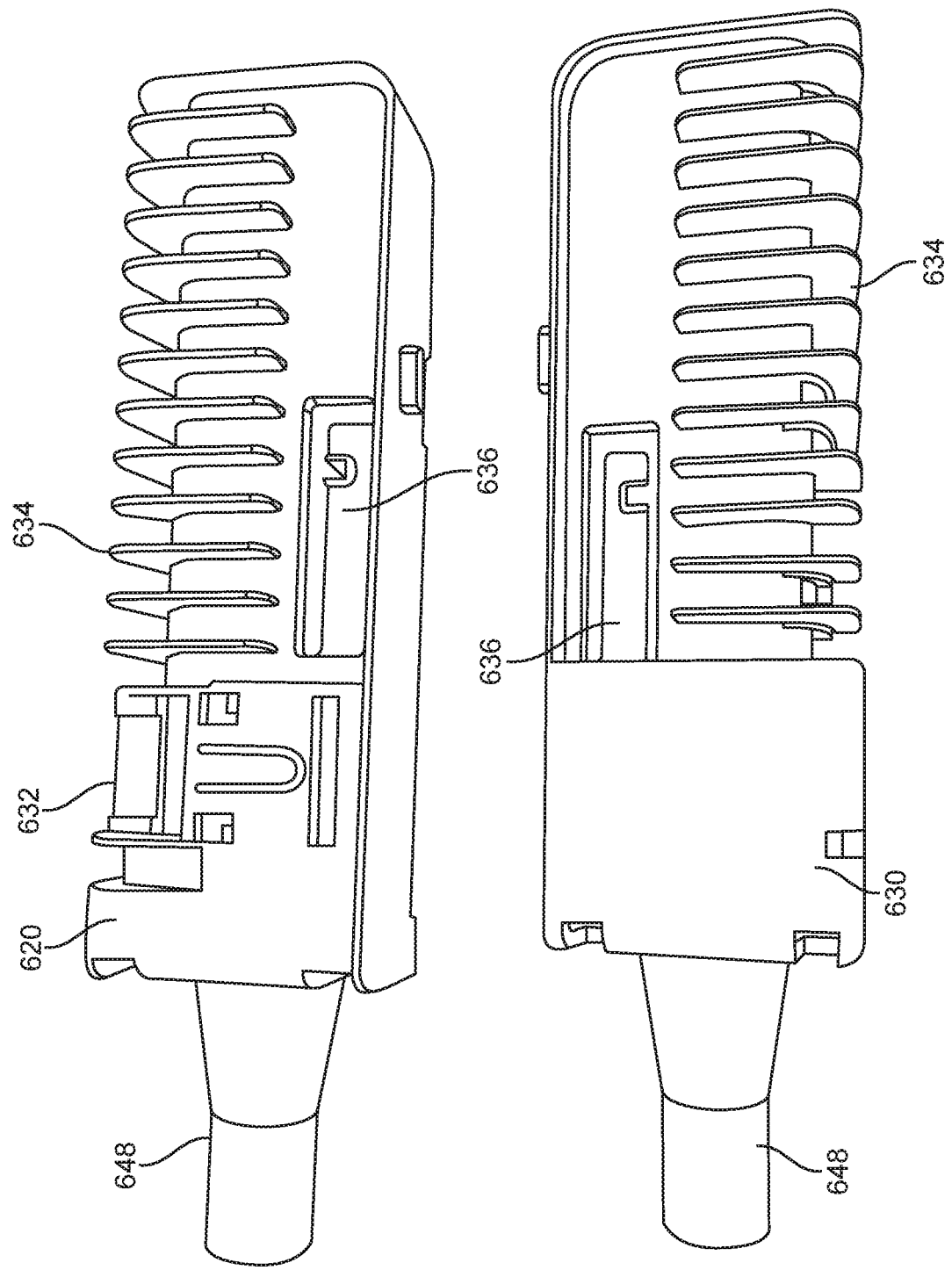
FIG. 15B is a perspective view of the right and left covers of the disposable cartridge assembly in accordance with an exemplary embodiment.
Figure 15C:
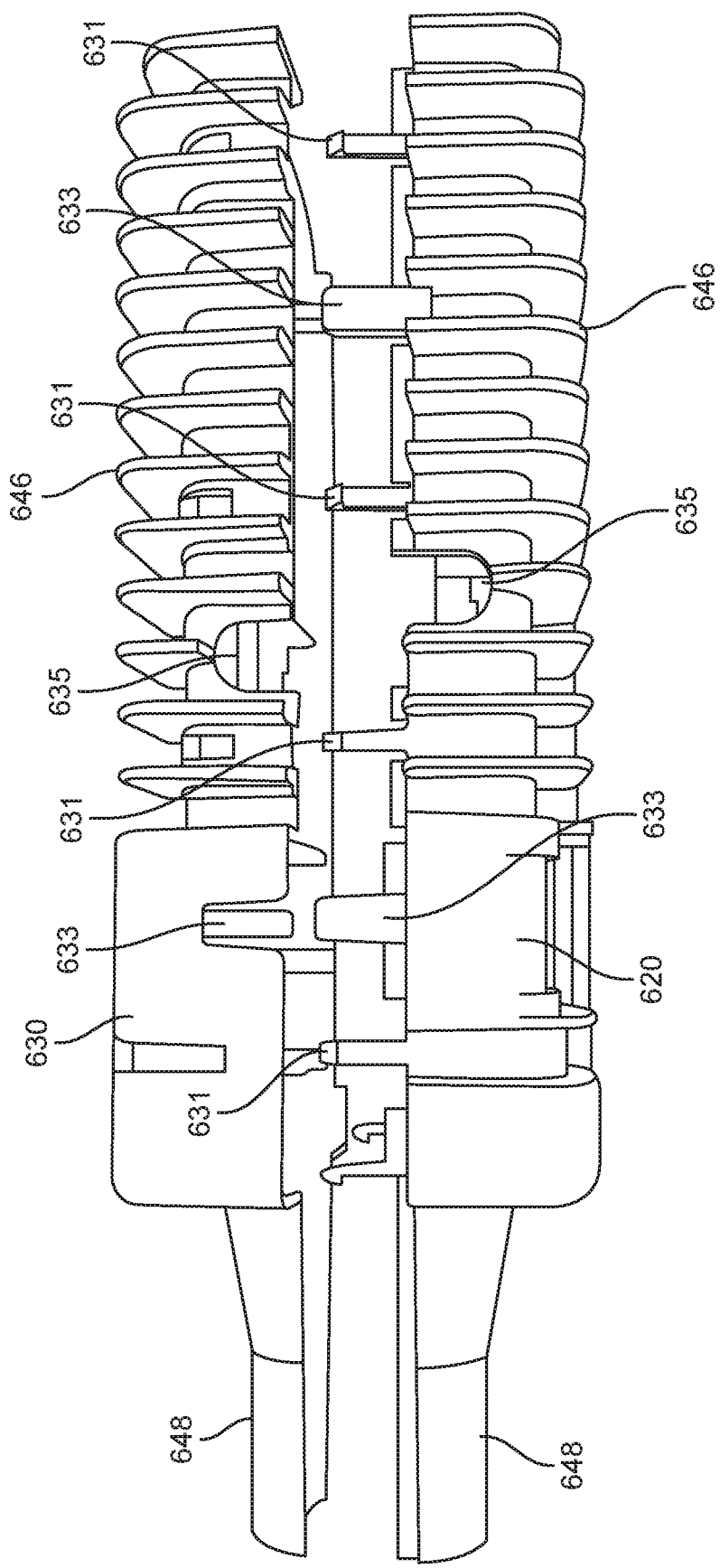
FIG. 15C is another perspective view of view of the right and left covers of the disposable cartridge assembly in accordance with an exemplary embodiment.
Figure 15D:
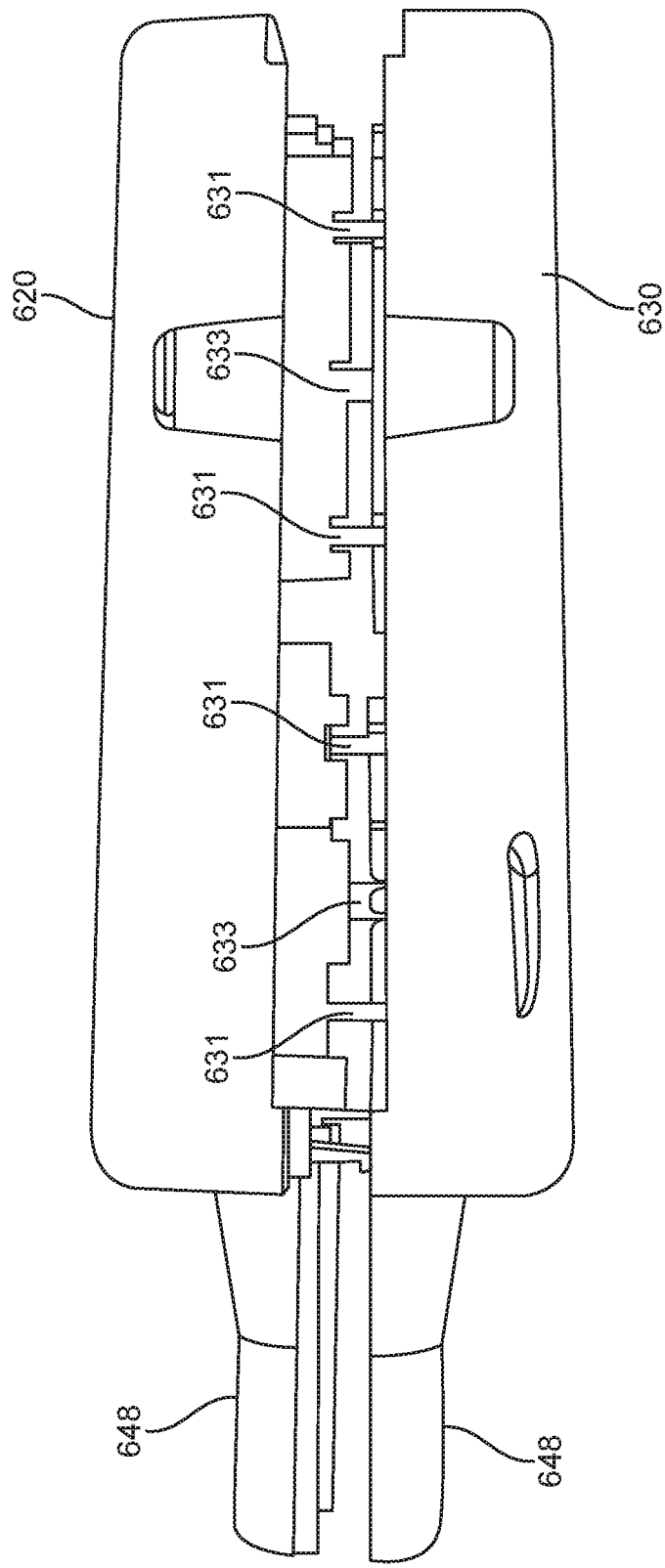
FIG. 15D is a further perspective view of view of the right and left covers of the disposable cartridge assembly in accordance with an exemplary embodiment.

In accordance with an exemplary embodiment, for example, upon insertion of the cartridge 500 into the starting position in the cartridge receiver) 400 as shown in FIG. 9A, the placement pins 418 (or a comparable other means) located within the cartridge receiver 400 move the latches 636 (see FIG. 15A and FIG. 15B) in the covers 620, 630 of the cartridge 500, releasing the active part of the cartridge 600 (FIG. 13) from the cartridge 500. In accordance with an exemplary embodiment, the active part of the cartridge 600 (or unshielded portion) includes the insulator 640, the capillary tube 650, and the susceptor 660 (See FIG. 12 and FIG. 13). The operator can then move the active part of the cartridge 600 by the handle 610 forward within the cartridge receiver 400 into an engaged or active position on a distal end or front portion 133 of the aerosol delivery unit 130 as shown in FIG. 9B for heating the susceptor 660 and thereby, heating the capillary tube 650 and aerosolizing the liquid formulation.

In accordance with an exemplary embodiment, the aerosol delivery system 100 is configured to interact with a device identifying card (or device ID card) 670 (see FIG. 12) on the cartridge 500 to determine, among other things, whether the cartridge 500 is new or previously been used. If the cartridge 500 has been used, the system 100 will not initiate or begin treatment. When a cartridge 500 has been used, the system 100 can mark the card 670 on the cartridge 500 as "read" electronically to prevent its re-use. The system 100 can also use the device ID card 670 to detect the presence of the cartridge 500 within the cartridge receiver 400.

In accordance with an exemplary embodiment, sensor 408A (see FIG. 7A) in the aerosol delivery unit 130 detects when the active part of the cartridge 600 is fully forward in the engaged position. In addition, as set forth above, the treatment or delivery of a drug will not begin until the active part of the cartridge 600 is in the fully engaged position. Once treatment has been initiated, the cartridge lock 458 (see FIG. 8A and FIG. 8B) closes to fix the position of the active part of the cartridge 600 within the cartridge receiver 400. In accordance with an exemplary embodiment, the active part of the cartridge 600 cannot be removed while the lock 458 is activated and the lock 458 will not open until treatment has been completed, stopped, or paused. The cartridge latch assembly 430 is moved into a locking position by the lock 458 electronically. The lock 458 includes a motor with a cam attached to the motor shaft within the aerosol delivery unit 130.

In accordance with an exemplary embodiment, as disclosed above, the system 100 (FIG. 1) uses an induction heating system, in which temperature of the capillary 650 and the susceptor 660 can be monitored via an infrared (IR) sensor 480 (see FIG. 8A and FIG. 10) on the infrared (IR) sensor board or assembly 454. In addition, both heating and sensing can be accomplished without direct physical contact with the active part of the cartridge 600.

Figure 12:
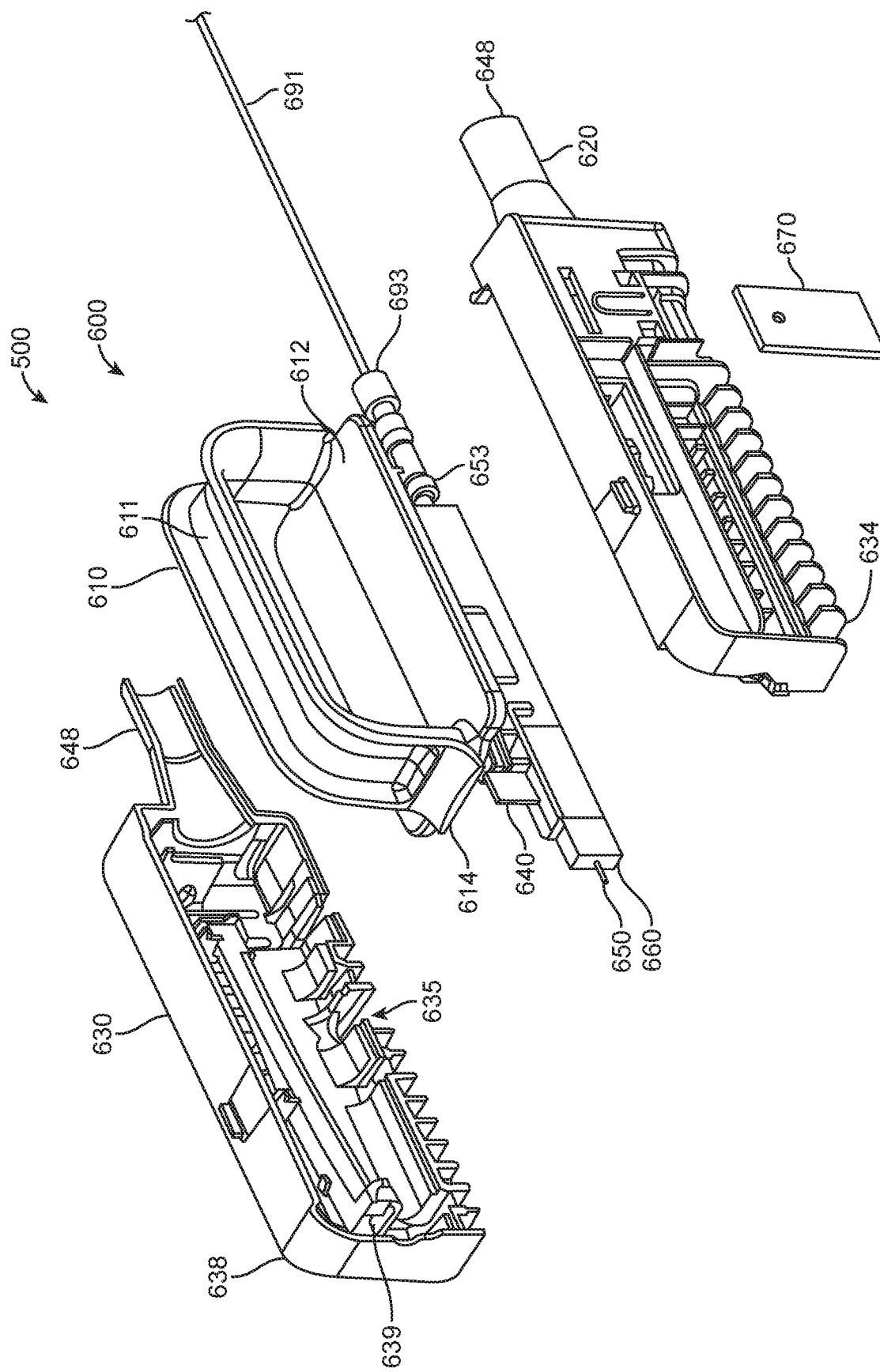
FIG. 12 is an exploded perspective view of a portion of the disposable cartridge assembly in accordance with an exemplary embodiment.
Figure 13:
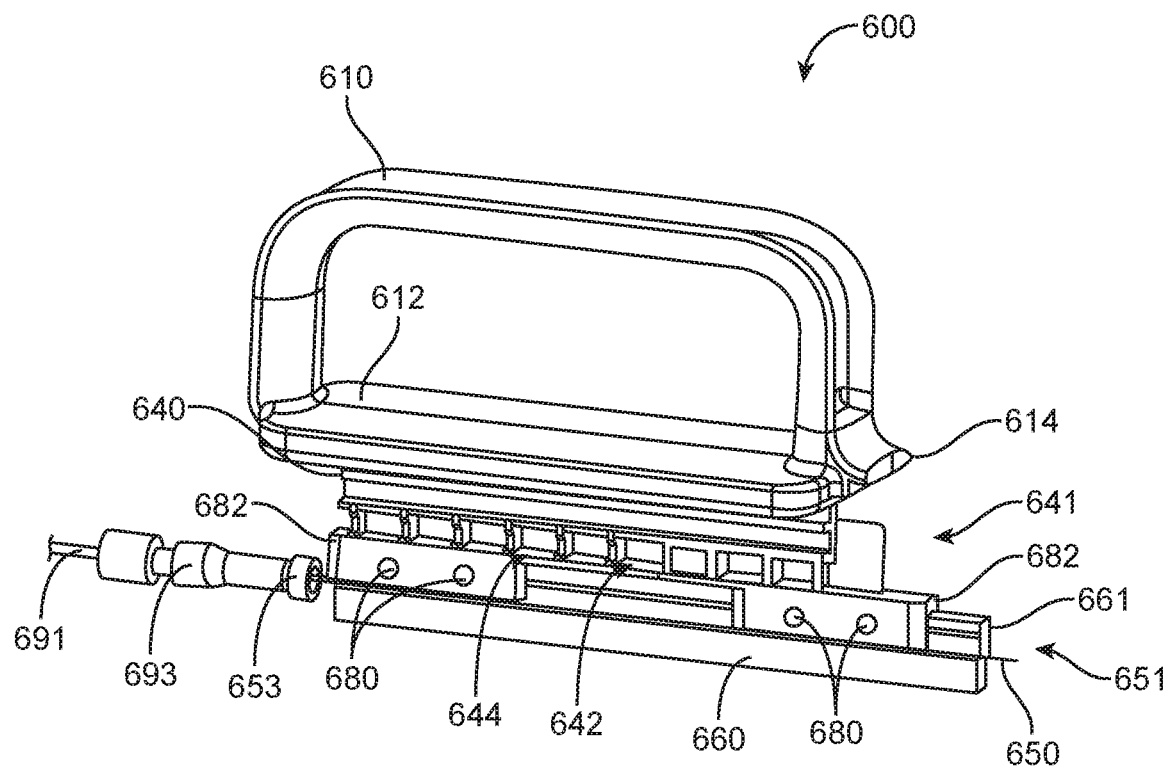
FIG. 13 is a perspective view of a portion of the disposable cartridge assembly in accordance with an exemplary embodiment.

In accordance with an exemplary embodiment, the induction heating system (FIG. 10) can provide evenly distributed heat to the drug delivery path and facilitate aerosolization. For example, in accordance with an exemplary embodiment, the drug temperature increases, for example, from room temperature to over 200° C. in less than 2 seconds. The drug delivery path passes through a capillary tube 650, which is embedded inside a conductive element, referred to as the susceptor 660 (FIG. 12 and FIG. 13). In accordance with an exemplary embodiment, the inductor 450 via induction heats the susceptor 660. Conductive, usually metallic, materials can be used to manufacture the susceptor 660.

In accordance with an exemplary embodiment, the temperature of the susceptor 660 can be monitored via an IR sensor 480 in the IR sensor board 454 (FIG. 10) and this signal can be used in a feedback control loop to precisely control the temperature of the susceptor 660. In accordance with an exemplary embodiment, a black coating can be applied to the susceptor 660 to provide a more consistent measurement surface, which could otherwise introduce variation.

Figure 10:
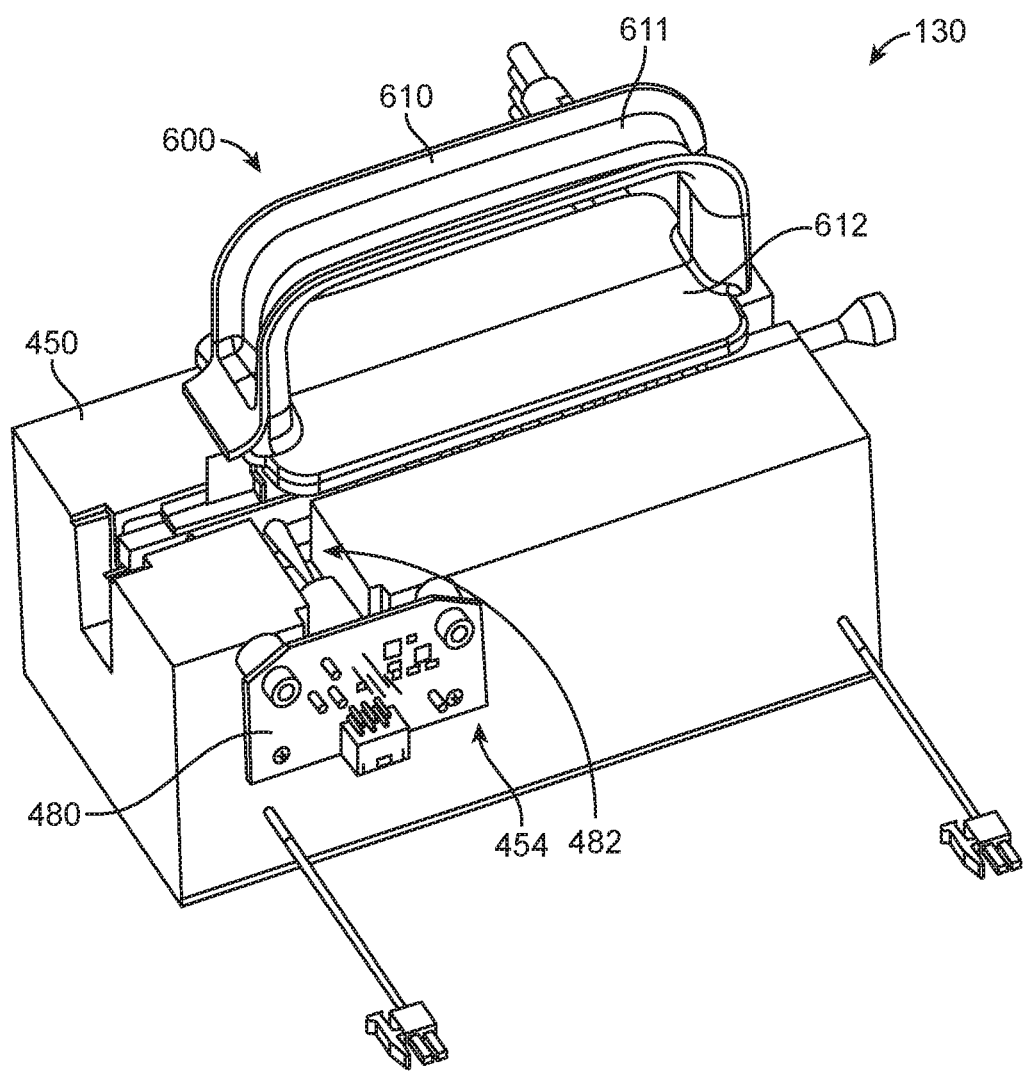
FIG. 10 is a perspective view of a portion of the disposable cartridge assembly and the aerosol delivery unit in accordance with an exemplary embodiment.

FIG. 10 is a perspective view of a portion of the cartridge, the active part of the cartridge (or the unshielded part of the cartridge) 600 inserted into the inductor 450 for heating in accordance with an exemplary embodiment. As shown in FIG. 10, the active part of cartridge 600 is configured to be received within the potted inductor 450, which includes an IR sensor board or assembly 454 having an IR sensor 480 for sensing the temperature range of the susceptor 660 during use, for example, 150° C. to 300° C., preferably, 200° C. to 250° C. In accordance with an exemplary embodiment, the active part of cartridge 600 can be self-aligning to the transition adapter 700, as the transition adapter 700 has some limited freedom to move about during engagement.

In FIG. 10, the active part of the cartridge 600 (the cartridge without the covers 620, 630) with the handle 610 and its flat plate portion 612 are shown along with the rest of the active part of the cartridge 600 being inside of the inductor. The groove 482 provides visibility to the IR sensor PCB assembly 454. Another groove 484 provides the alignment with the susceptor 660 (FIG. 13) in part, for the inductor 450 to properly heat the susceptor 660.

Figure 11:
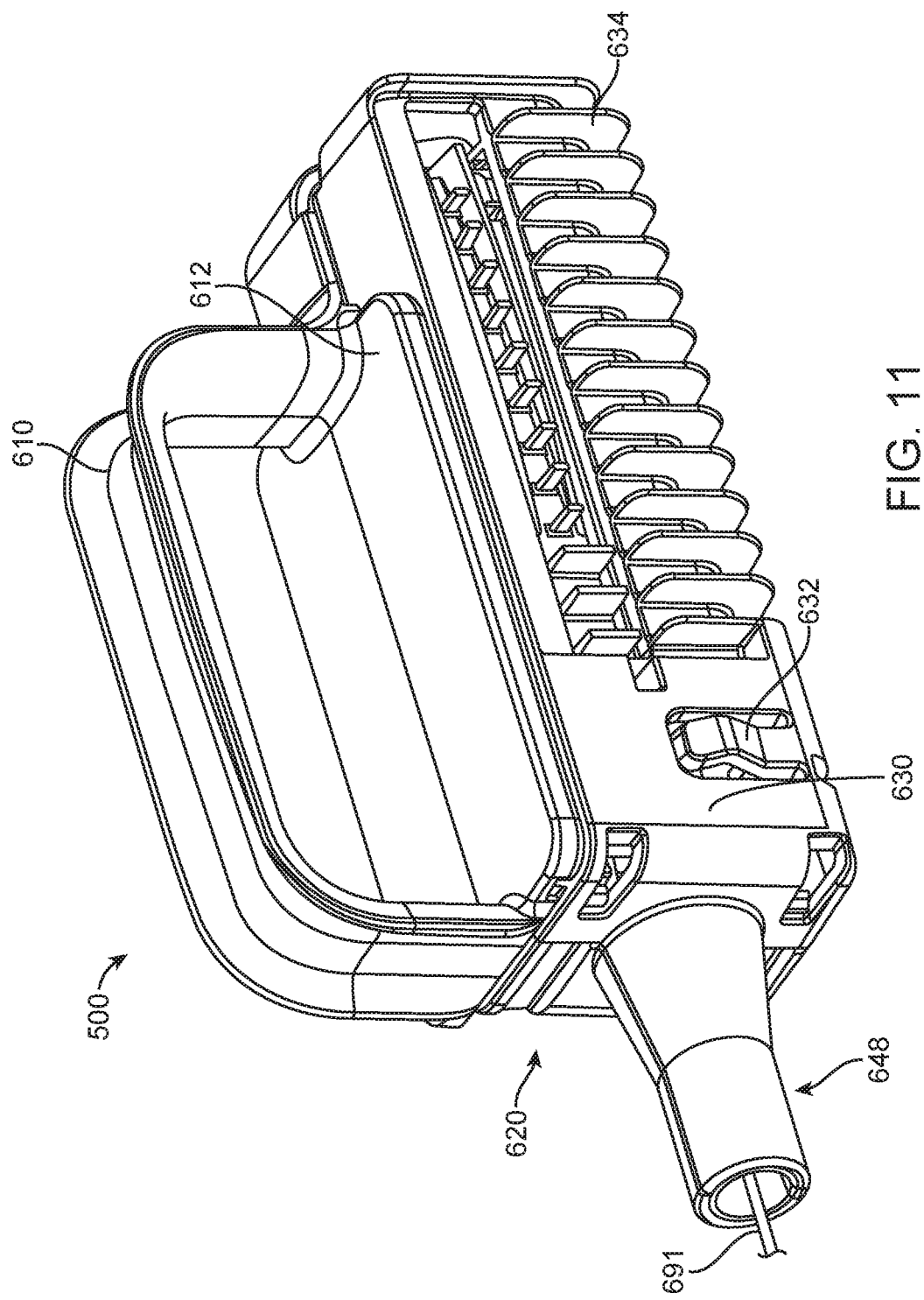
FIG. 11 is a perspective view of a portion of the disposable cartridge assembly in accordance with an exemplary embodiment.

FIG. 11 is a perspective view of a portion of the cartridge 500 in accordance with an exemplary embodiment. The cartridge assembly 500 can include a handle 610 and a relatively flat base plate 612, which is adjacent to a pair of covers 620, 630, for example, a right cover 620 and a left cover 630, an insulator 640, a capillary tube 650, a sleeve for tubing 648, tubing 691 for delivery of liquid drug into the capillary tube 650, and a susceptor 660. As shown in FIG. 11, the right and left covers 620, 630 can include a molded spring 632, which pushes or forces the cartridge and device identifying card (on opposite side) 670 (FIG. 12) against the cartridge identification PCB assembly 422 located on the aerosol delivery unit 130. Each of the right and left covers 620, 630 can include a plurality of heat dissipating fins 634, which also provide a space between the users grip of the handle 610, and the sometimes hot contents within the covers 620, 630 after use, for example, the capillary tube 650 and the susceptor 660.

FIG. 12 is an exploded perspective view of a disassembled cartridge 500 in accordance with an exemplary embodiment. As shown in FIG. 12, the cartridge 500 can include an oval or rectangular shaped handle 610 with a groove 611, the right cover 620, the left cover 630, an insulator 640, the capillary tube 650, the susceptor 660, the device identifying card 670, a sleeve for tubing 648, and optionally, the tubing 691 connected to the proximal end of the capillary for the delivery of the liquid drug to the capillary tube.

In accordance with an exemplary embodiment, it would be desirable that the mechanical features of the cartridge 500 are compact and protect the user from contacting with the heated capillary tube 650 and the susceptor 660 as shown in FIG. 12. For example, the covers 620 and 630 of the cartridge 500 can include heat dissipating features (for example, fins) 634 (FIGS. 15A-15D), which dissipate heat and creates space between the user and the hot components, for example, the heated capillary tube 650 and susceptor 660.

In accordance with an exemplary embodiment, the capillary tube 650 inside the cartridge 500 is part of the drug delivery path of the aerosol delivery system 100. In accordance with an exemplary embodiment, a new cartridge 500 is used for each drug treatment or for a portion of a drug regimen. The old (or used) cartridge 500 is removed and discarded, and a new cartridge 500 is installed into the aerosol delivery system 100. During treatment, for example, the capillary tube 650 and the susceptor 660 in the cartridge 500 can get very hot, for example, nearly 250° C. Thus, upon removing and while the cartridge 500 is out of the system 100 (for example, not in use), the hot surfaces must not be exposed. Additionally, delivery of the liquid formulation (or drug) cannot begin until the cartridge 500 can be fully installed into the cartridge receiver 400. In addition, the system 100 is preferably designed and configured such that the cartridge 500 cannot be removed while the liquid formulation (or drug) is being heated and delivered to a patient.

In accordance with an exemplary embodiment, a lock snap feature 638 on each of the covers 620, 630 (FIGS. 12, 15A) can help prevent the user from moving the active part of the cartridge 600 forward within the covers 620, 630 while it is nested on the placement pins 418 in the cartridge receiver 400 of the aerosol delivery unit 130. In addition, protective arms or latches 636 (FIG. 15A) can keep the active part of the cartridge 600 within the covers 620, 630, for example, in the event the disposable cartridge assembly 500 is dropped. A protective feature 639 (FIG. 12) on the front of the protective arms 636 as disclosed herein can also help prevent the user from being able to place their finger on the tip of the capillary tube 650. A molded spring 632 (see FIG. 11) biases the covers 620, 630, and the device identifying card 670 (see FIG. 12) toward the cartridge identification PCB assembly 422 (FIG. 7A). The cartridge 500 can include a protective sleeve 648 for tubing 691 into a proximal end 653 of the capillary tube 650 (FIG. 12).

In accordance with an exemplary embodiment, as shown in FIG. 12, the right and left plastic covers 620, 630 of the disposable cartridge assembly (or cartridge) 500 are configured to enclose the hot parts, for example, the capillary tube 650 and the susceptor 660. The covers 620, 630 can be locked into place, for example, with internal latches 636 (FIG. 15A and FIG. 15B). When the cartridge 500 is inserted into the starting position in the cartridge receiver 400 of aerosol delivery unit 130, the latches 636 are retracted by placement pins 418 (not shown), thereby, releasing the active part of the cartridge 600. Once the active part of the cartridge 600 is moved into the inductor 450, the covers 620, 630 are disengaged and left in the initial position at the proximal end 131 of the aerosol delivery unit 130. The user can then slide the active part of the cartridge 600 forward by the handle 610, engaging the susceptor 660 and the capillary tube 650 into the engaged position with the transition adapter 700. In accordance with an exemplary embodiment, sensors 408A, 408B can determine if the susceptor 660 and transition adaptor 700 are in the engaged position before drug delivery will begin. In accordance with an exemplary embodiment, the covers 620, 630 are preferably plastic, for example, a molded plastic.

In accordance with an exemplary embodiment, rather than being an oval or rectangular shaped handle, the handle 610 can be any suitable shape, which can easily insert and remove the disposable cartridge assembly 500 from the cartridge receiver 400.

FIG. 13 is a perspective view of a portion of the cartridge 500 in accordance with an exemplary embodiment. This portion is designated as the active part of the cartridge 600 and includes a handle 610, a flat portion of the handle 612, an insulator 640, a susceptor 660, a capillary tube 650 with a distal capillary tip 651 which will be connected to a transition adapter 700 (FIG. 18) and a proximal end of the capillary 653 connected to a tubing connector 693 and a tubing 691 (FIG. 11 and FIG. 12) for delivery of liquid drug to the capillary tube 650. In accordance with an exemplary embodiment, the active part of the cartridge 600 can have a sensor flag 641 located preferably on the distal end 641 of the insulator, which blocks the light so that the optical sensor 408B (FIG. 7A) is engaged to show that the connection between the susceptor 660 and the transition adapter 700 (FIG. 9A and FIG. 9B) has been made. In addition, the insulator 640 can include a sliding guide 646 (FIG. 14) configured to allow the active part of the cartridge 600 to slide in the active alignment groove 420 (FIG. 7A) as the active part of the cartridge 600 moves forward into the inductor 450.

As shown in FIG. 13 and FIG. 14, the insulator 640 can include one or more flanged or angular surfaces 682 with a plurality of wicking ports 680 for attaching the insulator 640 to the susceptor 660 with an epoxy. The epoxy can be conductive or non-conductive. In accordance with an exemplary embodiment, the handle 610 is attached to the flat portion 612 of the handle 610 and then to the insulator 640 using a heat staking technique. Alternatively, these parts can be made as one or two parts by molding or other known methods. In accordance with an exemplary embodiment, a plurality of cut-outs 644 are located between the insulator 640 and the one or more flanges or angled surfaces 682 and/or an upper surface 661 of the susceptor 660. The plurality of cut-outs 644 can be configured to help dissipate the heat transfer from the susceptor 660 to the handle 610.

FIG. 14 is another perspective view of a portion of the disposable cartridge assembly 500 in accordance with an exemplary embodiment. As shown in FIG. 14, the insulator 640 includes one or more wicking paths 690 on the inside of the insulator 640 to help spread the conductive epoxy along the susceptor 660 (not shown). In addition, the insulator 640 can include a pin lock slot or notch 642 on each side. In accordance with an exemplary embodiment, the placement pins 418 located in the distal end of the cartridge receiver 400 have an additional function of releasing the covers 620, 630 when the cartridge 500 is placed in the initial position. It is also possible to use a separate set of pins or comparable items to unlock and release the covers 620, 630. Each cover 620, 630 has a placement pin access slot 635 to allow the placement pin 418 to go in when the cartridge 500 is placed into the initial position. The placement pin and the locking pin 418 can be referred to interchangeably.

FIGS. 15A-15D are perspective views of a cover 620, 630 of the disposable cartridge assembly 500 in accordance with an exemplary embodiment. In accordance with an exemplary embodiment, each of the covers 620, 630 can include a plurality of heat dissipating features (e.g., fins) 634. At least one of the covers 620, 630 can have one or more, preferably four, snap features 631 which would snap into a corresponding indentation or opening in the opposite cover such that both covers would come together to enclose the active part of the cartridge 600 (FIG. 13). In addition, at least one of the covers 620, 630 can have one or more, preferably two, overlapping snap features 633 to further ensure the integrity of the enclosure of the active part of the cartridge within the covers. In addition, one of the covers 620, 630, can include latches 636 configured to engage the insulator 640 by catching the pin notch lock 642 (FIG. 14), and which can help prevent the user from moving the active part of the cartridge 600 forward.

In accordance with an exemplary embodiment, the placement pins 418 in the cartridge receiver 400 of the aerosol delivery unit 130 release (or unlock) the active part of the cartridge 600 from the covers 620, 630 once the disposable cartridge 500 has been nested or correctly positioned within the cartridge receiver 400. When the cartridge 500 is placed on the placement pins 418 (FIG. 7B), the placement pins 418 go through the placement pin access slot 635 and disengage the covers 620, 630 from the active part of the cartridge 600 by pushing away the latches 636 and release the catch of the latches from the pin lock notches 642. Once the active part of the cartridge 600 is released, the covers 620, 630 continue to stay together. When the active part of the cartridge 600 is returned into the covers 620, 630, the cartridge 500 can be lifted off the placement pins. The placement pins 418 then release the latches 636 and the lock snap feature 638. In accordance with an exemplary embodiment, at least one of the covers 620, 630 contains a data card retainer 671 to hold the data card 670. One or more alignment pins 637 is located below the inner edge 643 of one or each of the covers 620, 630. The alignment pin 637 works with the sliding guide 646 (FIG. 14) on the insulator 640 and helps to guide the active part of the cartridge 600 into the alignment groove 420 (FIG. 9A).

Figure 16A:
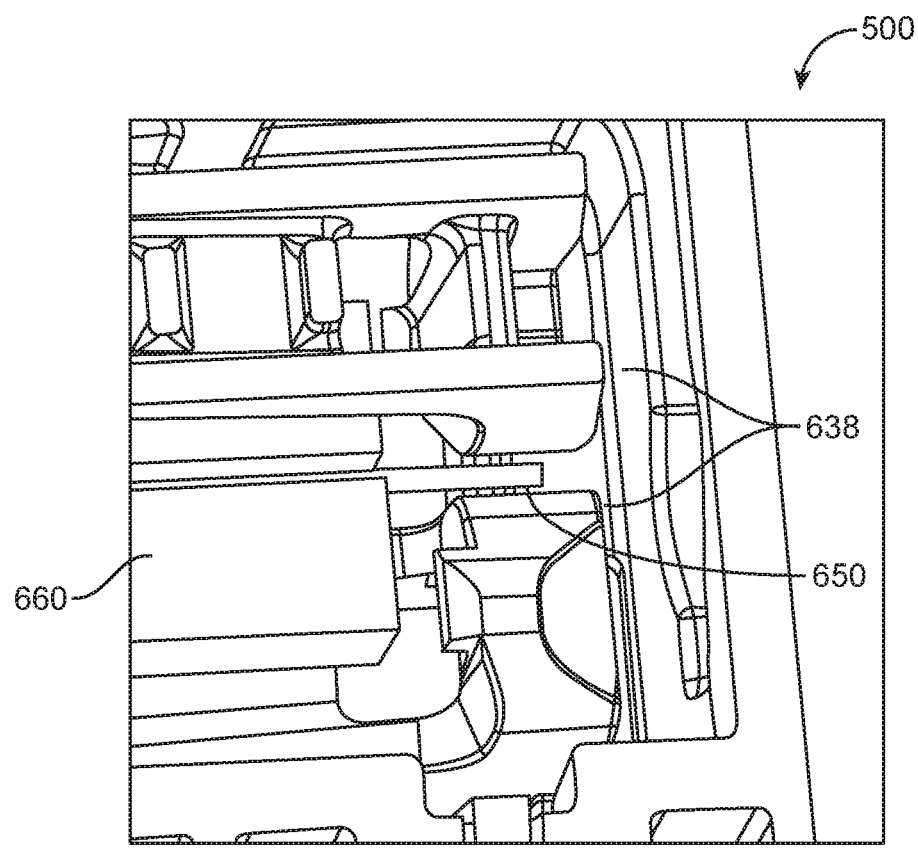
FIG. 16A is a perspective view of an inner portion of the disposable cartridge assembly in accordance with an exemplary embodiment.
Figure 16B:
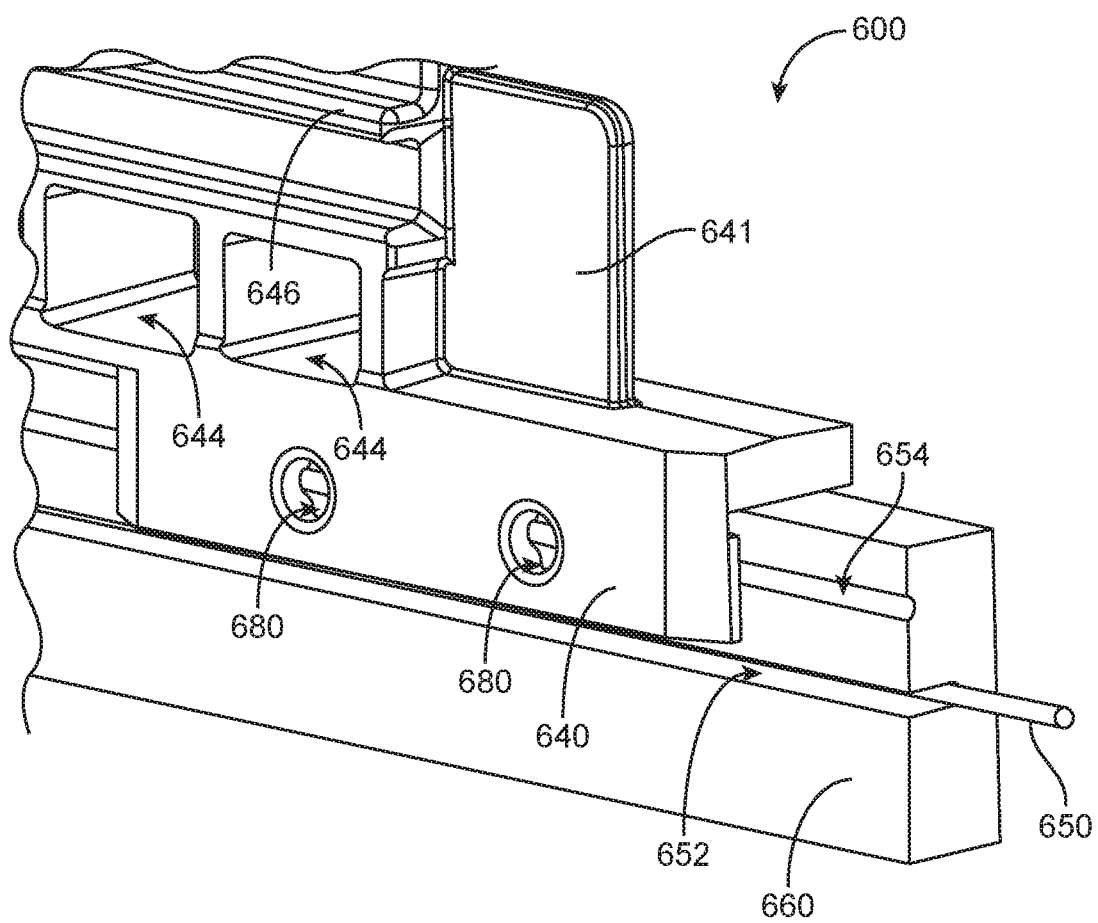
FIG. 16B is a perspective view of a portion of the disposable cartridge assembly in accordance with an exemplary embodiment.

FIG. 16A is a perspective view of an inner portion of the disposable cartridge assembly 500 in accordance with an exemplary embodiment. FIG. 16B is a view of a portion of the susceptor 660, the capillary 650 and the insulator 640. As shown in FIG. 16A, both of the lock snap features 638 (see also FIG. 12 and FIG. 15) on the right and left covers 620, 630, extend out in front (i.e., distal end) of the capillary tube 650 to prevent the user from, for example, poking a finger into the area of the tip 651 of the capillary tube 650 and getting burned. For example, the protective arms 638 provide this protection further enhanced by the addition of the protective feature 639 (FIG. 15). The lower arm 638 can wrap around the front end or portion (i.e., distal end) of the susceptor 660 in the normal position, for example, the upper protective arm 638 can be positioned above the capillary tube 650, and the lower protective arm 636 can be located alongside the capillary tube 650.

Figure 14:
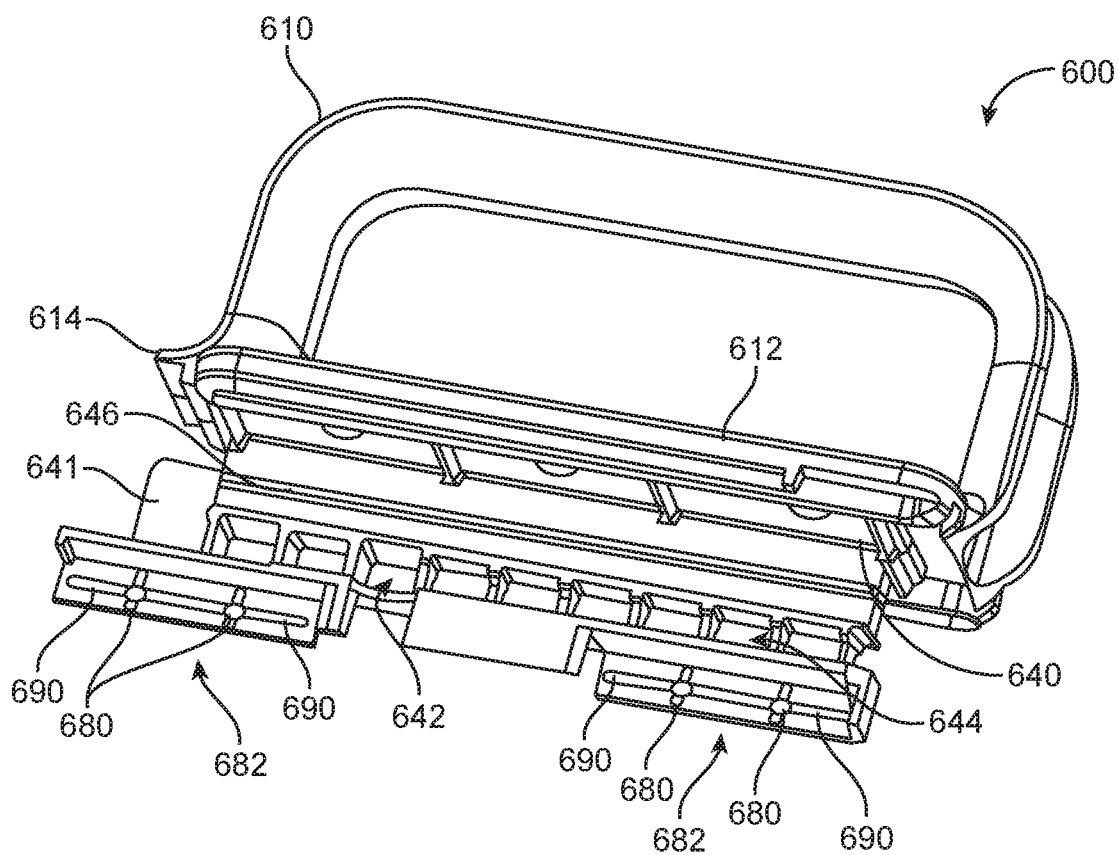
FIG. 14 is another perspective view of a portion of the disposable cartridge assembly in accordance with an exemplary embodiment.

FIG. 16B taken together with FIG. 14 show the connection of the susceptor 660 with the insulator 640. The susceptor 660 has a first groove 652 for the placement of the capillary 650. Preferably, the capillary 650 can be secured within the first groove by the application of conductive epoxy. The susceptor 660 has a second groove 654 which is configured to align with the wicking paths 690 of the insulator 640 in (FIG. 14) forming a hollow structure. When the epoxy is applied through the wicking ports 680, the epoxy spreads inside the hollow structure. When the epoxy is solidified, it forms a lock holding the susceptor 660 and the insulator 640 together. The epoxy does not have to be an adhesive.

In accordance with an exemplary embodiment, since a replaceable cartridge 500 can be a critical component in a drug delivery system, it is preferable that a new cartridge 500 is used for every treatment and disposed of afterwards. In addition, the susceptor 660 within the cartridge 500 can reach up to 300° C. or higher while administering the aerosol. Upon completion of the treatment, the cartridge 500 may need to be removed immediately from the aerosol delivery unit 130, before the cartridge 500 has had time to cool to a safe temperature. Therefore, as disclosed herein, measures need to be taken to prevent exposure to the user of the capillary tube 650 and the susceptor 660 of the cartridge 500 immediately following use.

Figure 17:
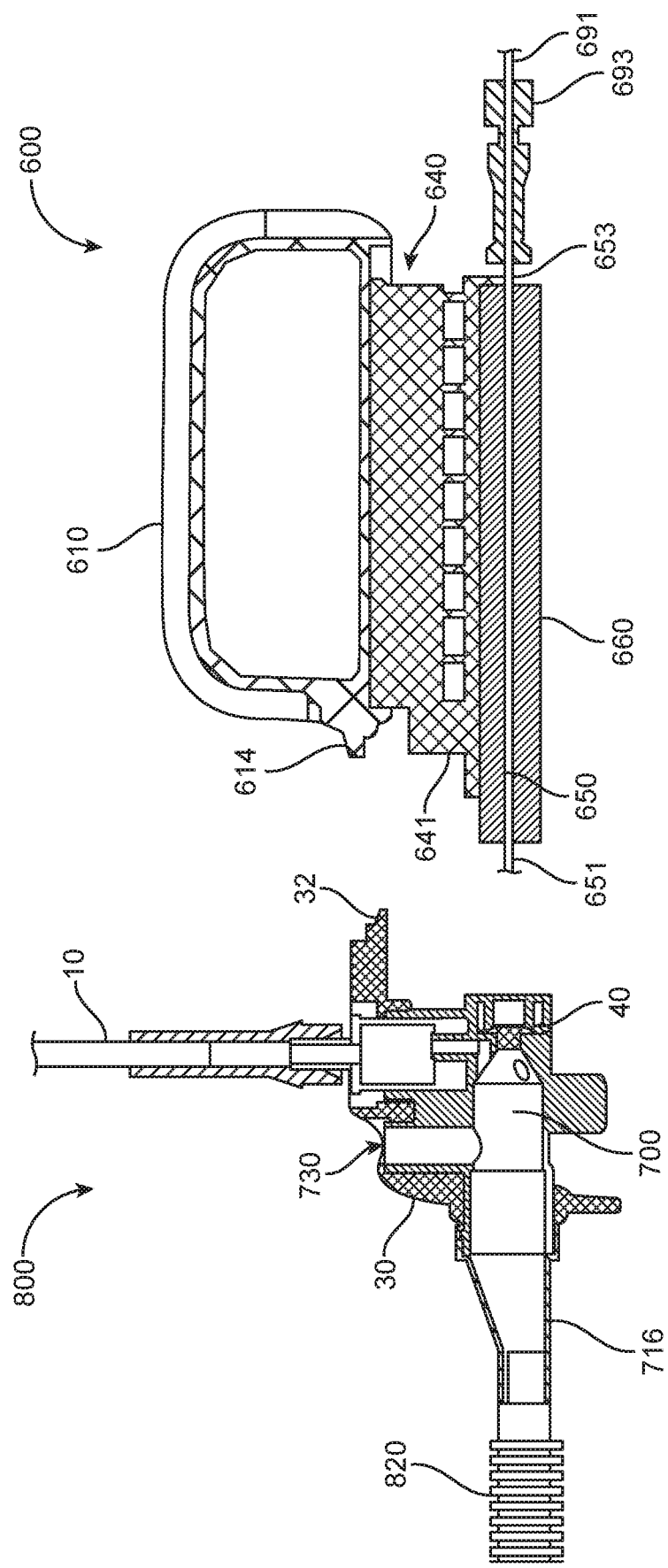
FIG. 17 is a cross-sectional view of a portion of the disposable cartridge assembly and transition adapter in accordance with an exemplary embodiment.

FIG. 17 is a cross-sectional view of the active part of the cartridge 600, the transition adapter 700, and a portion of the tube set assembly 800 in accordance with an exemplary embodiment. As shown in FIG. 17, a disposable tube set assembly 800 can include the transition adapter 700, a carrier gas tubing 10, a transition adapter cover 30, a capillary seal 40, a transition adaptor fitting 716 which connects the transition adaptor 700 with the first tubing 820. The disposable tube set assembly 800 is further described in detail below and shown in FIG. 22

A tubing 691 for delivery of liquid drug to the capillary tube (FIG. 17) preferably includes a high pressure tubing, which extends from the syringe pump unit 140 (FIG. 1) to a proximal end of the cartridge 500. The high pressure tubing assembly can include the tubing connection 693, which is configured to engage with the proximal end 653 of the capillary tube 650.

In accordance with an exemplary embodiment, the transition adapter 700 installs into a transition adapter cavity 414 (FIG. 6) in the cartridge receiver 400. When the active part of the cartridge 600 slides forward to engage with the transition adapter 700 and the transition adaptor cover 30, the front edge of the handle 614 of the active part of the cartridge 600 captures the cover edge 32 of the cover of the transition adapter and thereby engages the transition adapter 700 (FIG. 17). In accordance with an exemplary embodiment, sensor(s) 408A (FIG. 7A) detects the position of the active part of the cartridge 600 and the presence of the transition adapter 700 such that the system 100 will not initiate treatment if both the active part of the cartridge 600 and the transition adapter 700 are not detected. Once initiated, for example, in accordance with an exemplary embodiment, the lock 458 backs up the spring loaded cartridge latch assembly 430 to prevent the cartridge 500 from being removed.

Figure 7A:
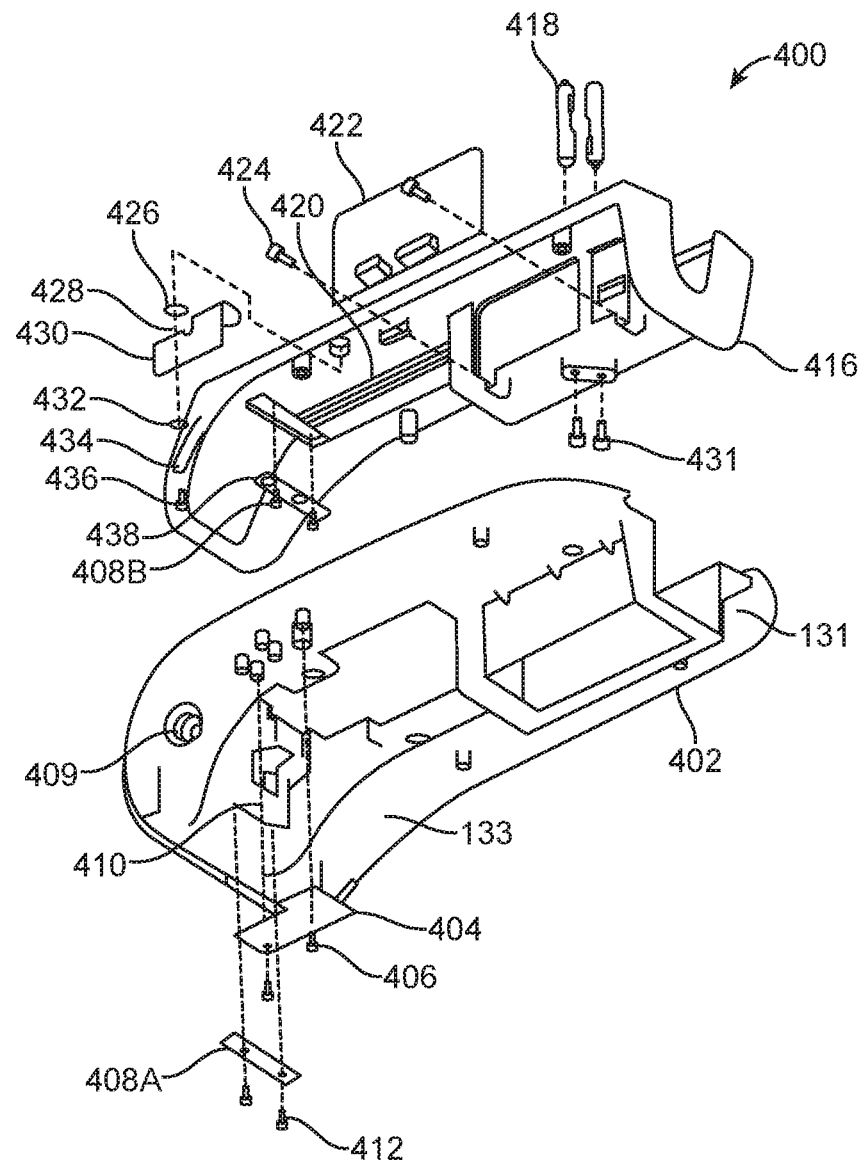
FIG. 7A is an exploded perspective view of a portion of the aerosol delivery unit in accordance with an exemplary embodiment.
Figure 7B:
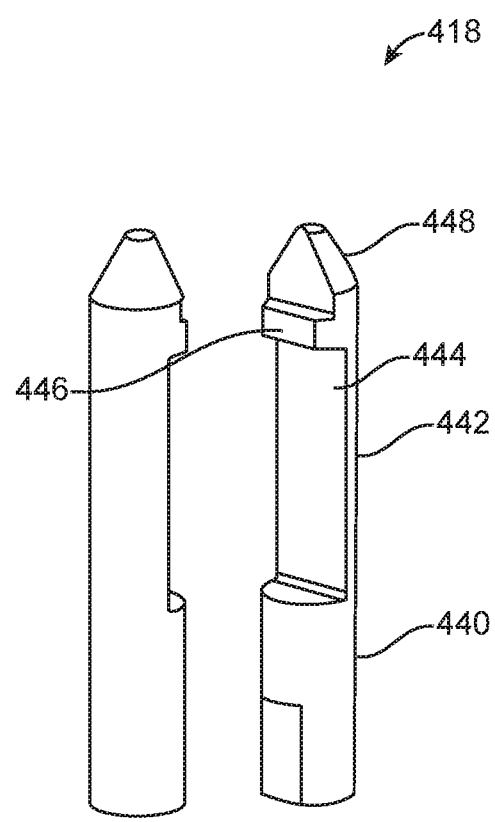
FIG. 7B is a perspective view of a pair of locking pins in accordance with an exemplary embodiment.
Figure 8B:
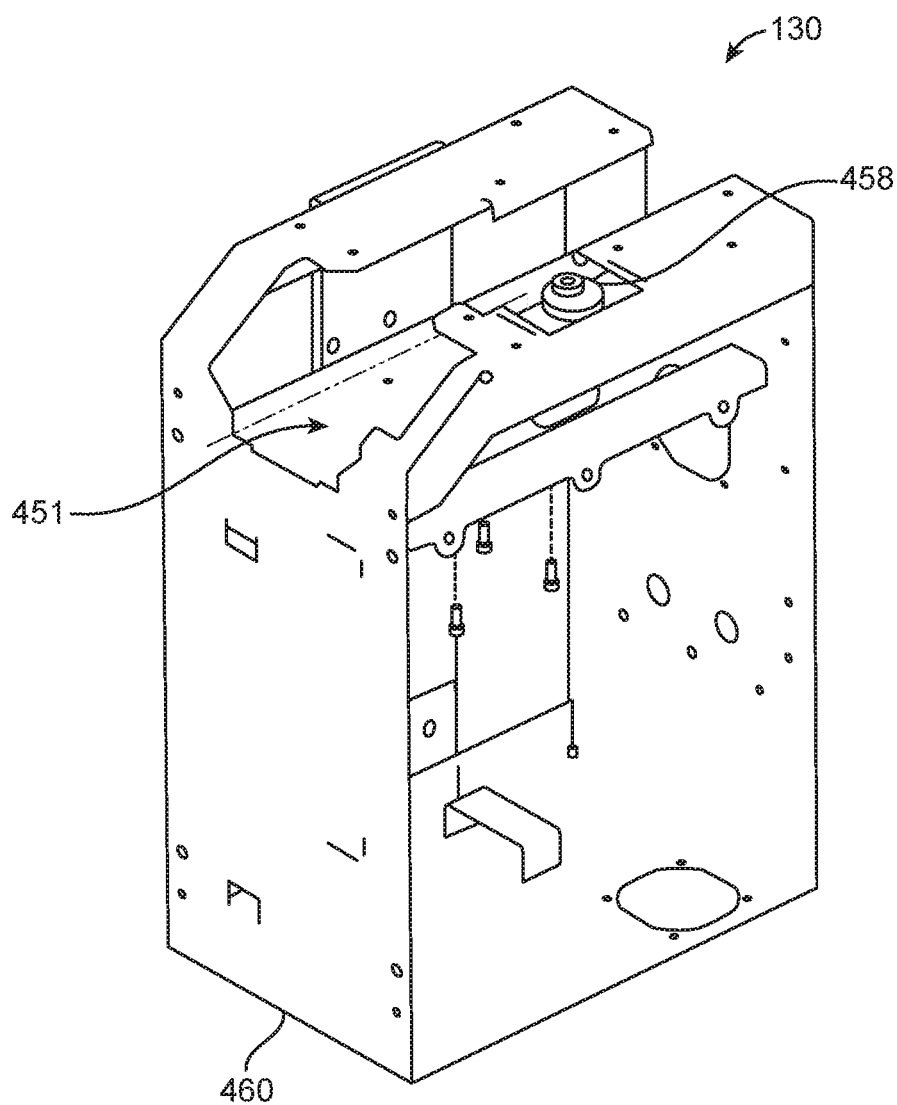
FIG. 8B is a perspective view of cartridge receiver of the aerosol delivery unit in accordance with an exemplary embodiment.
Figure 8C:
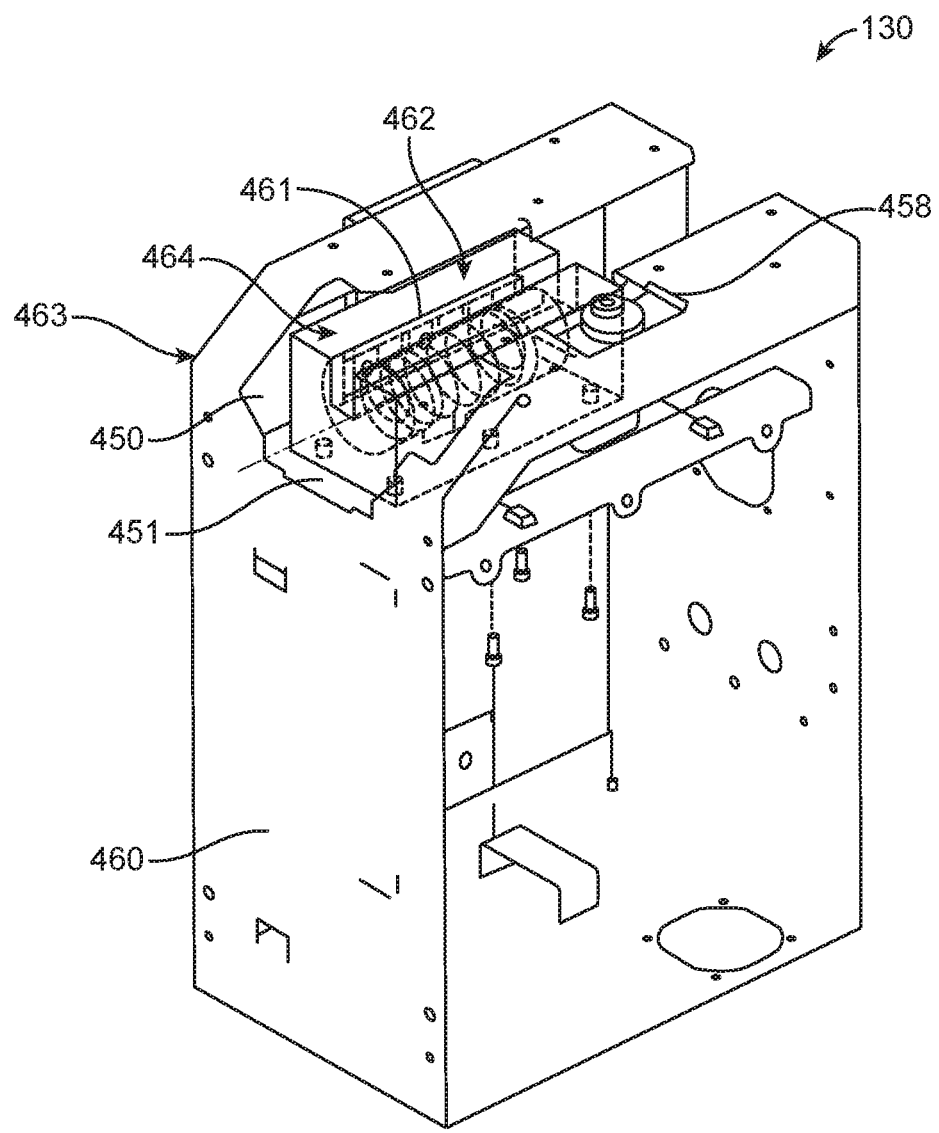
FIG. 8C is a perspective view of another portion of the aerosol delivery unit in accordance with an exemplary embodiment.
Figure 18:
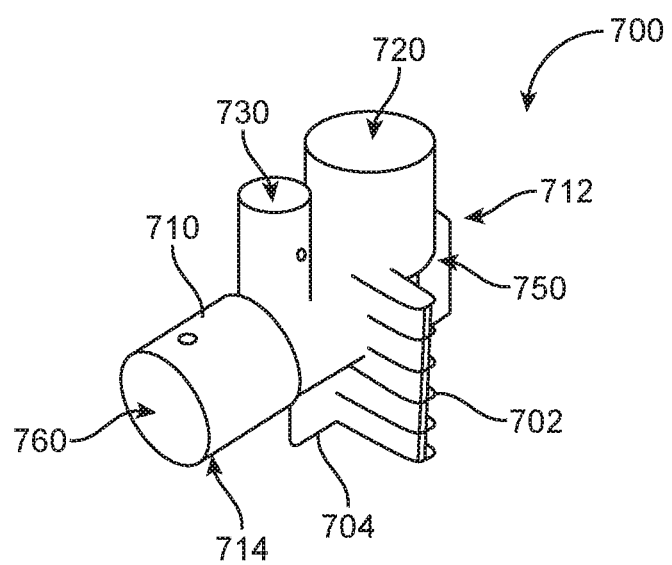
FIG. 18 is a perspective view of the transition adapter in accordance with an exemplary embodiment.

FIG. 18 is a perspective view of the transition adapter 700 in accordance with an exemplary embodiment. As shown in FIG. 18, the transition adapter 700 includes a housing 710 having an air admixing port 720, a temperature probe port 730, an input port 750, and an exit port 760. In addition, the transition adapter 700 can include a flange or extension portion 702, which is configured to be received within a distal end of the aerosol delivery unit 130. In addition, the transition adapter 700 has a flag 704 which works together with the light sensor 408A (FIG. 7A). When the transition adapter 700 is installed into the transition adapter cavity 414 on the aerosolizing device's cartridge receiver 400, the flag 704 enters the placement groove 426 (see FIG. 6) which signals the proper placement of the transition adaptor 700 by the light sensor 408A (FIG. 7A).

FIGS. 19-21 are cross-sectional views of the transition adapter 700 in accordance with an exemplary embodiment. As shown in FIGS. 18-21, the transition adapter 700 includes a housing 710 having a proximal end 712 and a distal end 714. The proximal end 712 has an aerosol passage or entry port 750 for receiving an aerosol produced by the heated capillary tube 650 of the active part of the cartridge 600. The aerosol passage or entry port 750 preferably includes a capillary seal 40, which contains a connection to a distal tip of the capillary 651. The aerosol enters into an inner cavity 770 (FIG. 19) within the transition adapter 700 through the aerosol passage 750 where the aerosol is at least partially encircled and carried forward by parallel streams of carrier gas, which are originated from a source of gas or ventilator (not shown) and introduced into the transition adapter through at least one gas entry port 720, or alternatively, a plurality of gas entry ports to form an entrained aerosol, which is a combination of the aerosol and the carrier gas. The carrier gas is preferably a non-humidified gas.

As shown in FIGS. 18-21, the aerosol passage 750 has a capillary seal 40, which receives the distal end of the capillary tube 651, which is positioned within a cavity on the proximal end 712 of the housing 710. The housing 710 preferably includes a generally cylindrical proximal portion 712, a cylindrical distal portion 714, and a carrier gas connection port 720 extending perpendicular to the proximal end 712 and configured to receive a carrier gas line 10 (FIG. 17), which transports a stream of carrier gas from the gas source or a ventilator to the transition adapter 700.

FIG. 19 is a side view of the transition adapter 700 as shown in FIG. 18 in accordance with an exemplary embodiment. As shown in FIG. 19, the housing 710 of the transition adapter 700 has a cylindrical proximal portion and a cylindrical distal portion, which extend from the proximal end to the distal end of the housing 710. In accordance with an exemplary embodiment, an outer diameter of the cylindrical proximal portion is smaller than an outer diameter of the cylindrical distal portion. The housing 710 of the transition adapter 700 includes a cylindrical body, which includes a carrier gas connection port 720 for receiving the carrier gas via a carrier gas line from a ventilator or a gas source. The carrier gas connection port 720 has a cylindrical cross-section, which is in communication with a plurality of gas entry ports and a plurality of corresponding gas exit ports 772 via a passage. Each of the gas exit ports 772 delivers a stream of carrier gas to the inner cavity 770 of the transition adapter 700. A temperature probe port 730 is located on an upper portion of the transition adapter 700 and arranged between the carrier gas connection port 720 and a distal end 714 of the transition adapter 700. The temperature probe port 730 is located at the top of the transition adapter's aerosol and carrier gas mixing chamber and can provide access to a temperature probe 160 (FIGS. 1-3A) to assess the temperature of the entrained aerosol as an indicator of the aerosol delivery system operation.

In accordance with another exemplary embodiment as shown in FIGS. 19-21, the source of gas can be introduced into the inner cavity 770 via a single gas entry port and a single gas passage. In accordance with an exemplary embodiment, rather than multiple or a plurality of passages or conduits for introducing the gas stream into cavity 770, the separation of gas streams into the inner cavity 770 can be performed through a plurality of openings or exit ports along the conical section 780. In accordance with an exemplary embodiment, the transition adapter 700 can be configured as shown in commonly-owned U.S. Patent Publication No. 2014/0053831 A1, which is incorporated herein in its entirety.

In accordance with an exemplary embodiment, the transition adapter 700 installs into the aerosol output pocket 410 on the cartridge receiver 400 (FIG. 6) located at the distal end 133 of the aerosol delivery unit. The cartridge 500 with the attached tubing for delivery of liquid drug to the capillary 691 is placed in the cartridge receiver 400 and slides forward to engage with the transition adapter 700 arranged on the distal side 133 of the cartridge receiver 400 of the aerosol delivery unit 130. The susceptor 660 within the cartridge 500 can be self-aligning to the transition adapter 700, as the transition adapter 700 has some limited freedom to move about during engagement. In accordance with an exemplary embodiment, the handle 610 of the active part of the cartridge 600 can capture or engage a cover of the transition adapter 700 and thereby captures the transition adapter 700. As set forth above, sensor(s) 408A and 408B monitor the position of the active part of the active part of the cartridge 600 and presence of the transition adapter 700 in the cartridge receiver 400. In accordance with an exemplary embodiment, the system 100 will not initiate treatment if both the active part of the cartridge 600 and the aerosol transition adapter 700 are not detected. Once initiated, an electronically controlled interlock 458 closes to prevent the active part of the cartridge 600 from being removed.

Figure 22:
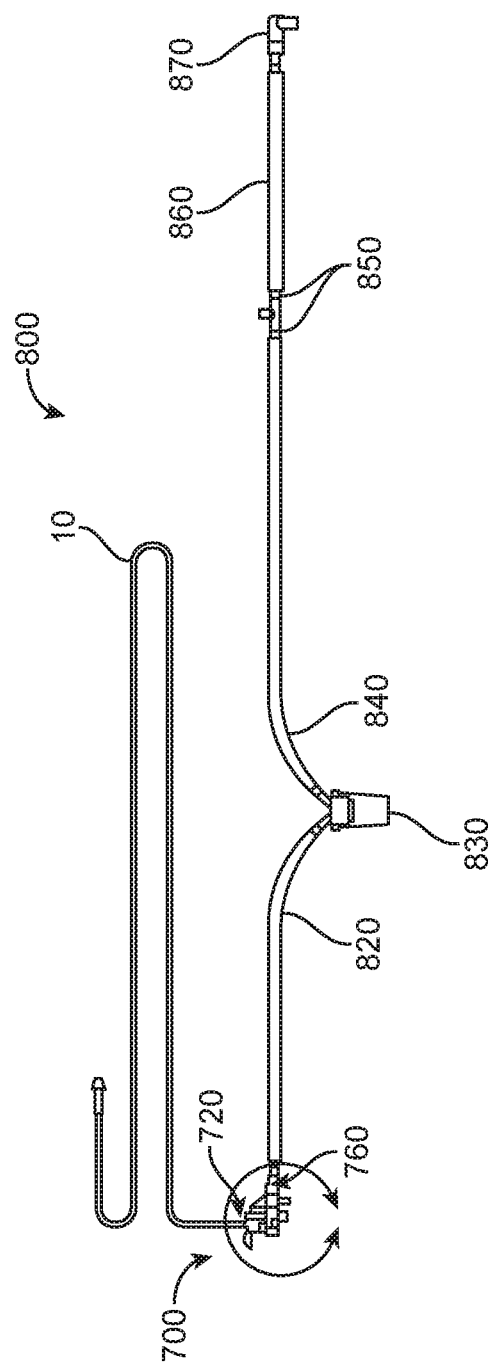
FIG. 22 is a cross-sectional view of a tube set assembly in accordance with an exemplary embodiment.

FIG. 22 is a cross-sectional view of a tube set assembly 800 in accordance with an exemplary embodiment. A carrier gas tube 10 is configured to deliver a carrier gas from a source to the carrier gas entry port 720 of the transition adaptor 700. As shown in FIG. 22, a disposable aerosol tube set 800 includes the carrier gas tube 10, the transition adapter 700, a transition adapter cover 30, and a capillary seal 40 (FIG. 17), a first piece of tubing 820, the transition adaptor fitting 716 which connects the transition adaptor 700 with the first tubing 820, a condensation trap 830 and a second piece of tubing 840. The carrier gas tube 10 delivers the carrier gas to the transition adaptor 700 where the carrier gas meets with the aerosol delivered from the capillary (not shown) to form an entrained aerosol. The entrained aerosol enters the first piece of tubing 820, passes by the condensation trap 830, and then enters into the second piece of tubing 840, which can be connected to a patient interface (not shown). The disposable aerosol tube set 800 can further include a tee adapter 850 for a temperature probe connected to the second tubing 840, a third tubing 860 and an elbow connector 870 for connecting to a patient interface (not shown).

In accordance with an exemplary embodiment, both tubing 691 together with the tubing connector 693 and the tube set 800 are preferably replaceable. For example, in accordance with an exemplary embodiment, the tube set 800 can be used once per patient, while the tubing 691 (FIG. 17) can be replaced with each dose. Therefore, the tubing 691 is changed with greater frequency and needs to be removable without upsetting the tube set 800, which drives the requirement that the tube set assembly 800 be installed first, before the tubing 691. Additionally, during treatment, neither the tubing 691 nor the tube set 800 can be removed.

Figure 23:
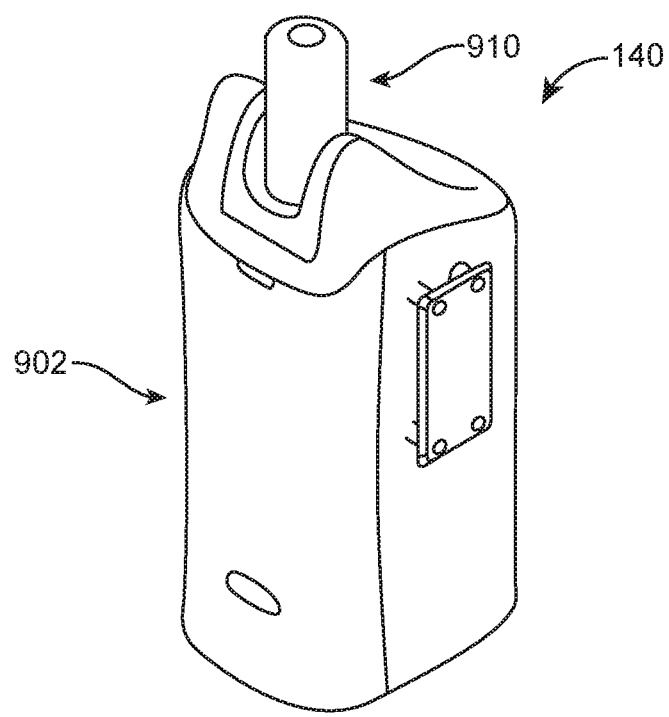
FIG. 23 is a perspective view of the syringe pump unit in accordance with an exemplary embodiment.

FIG. 23 is a perspective view of the syringe pump unit 140 in accordance with an exemplary embodiment. As shown in FIG. 23, the syringe pump unit 140 can include a housing 902, which is configured such that an operator can load, for example, a disposable syringe 900 (FIG. 24) into the syringe holder 910. The disposable syringe can hold from 20 ml to 200 ml of liquid drug. In accordance with an exemplary embodiment, the syringe holder 910 pivots on a hinge to expose the opening on the bottom of the syringe holder 910. In accordance with an exemplary embodiment, the syringe holder 910 is preferably a clear plastic. The syringe 900 is aligned and inserted into the syringe holder 910. Then, the syringe holder 910 is pivoted back to its original position. In accordance with an exemplary embodiment, an indicator light (not shown), for example, a green indicator light(s) can convey to the operator that the syringe holder 910 is closed and ready for use.

Figure 24:
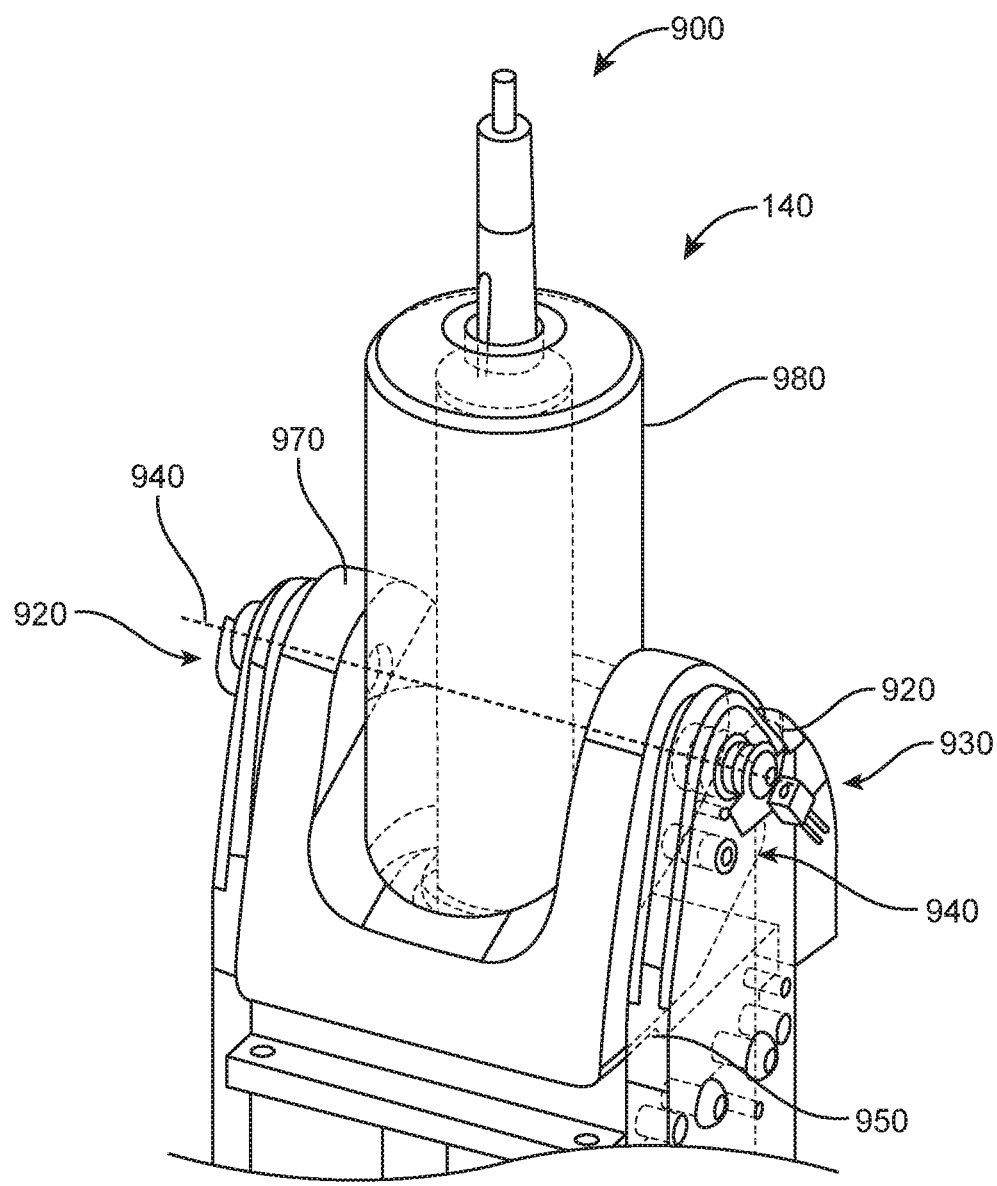
FIG. 24 is a perspective view of the syringe pump unit in accordance with an exemplary embodiment.

FIG. 24 is a perspective view of the syringe pump unit 140 in an operational state accordance with an exemplary embodiment. As shown in FIG. 24, the syringe pump unit 140 can include an approach for loading and supporting a syringe 900 in a syringe pump 910, which is especially suited for a high pressure syringe pump. In accordance with an exemplary embodiment, a plunger 960 (FIG. 25) presses on the piston (not shown) in the syringe 900, pressurizing the fluid in the syringe 900, which creates a net force coaxial with the syringe 900. In accordance with an exemplary embodiment, a structure, such as the syringe pump holder 910 is needed to hold the syringe 900 in place when the force is applied. In addition, the syringe pump holder 910 should also allow the syringe 900 to be inserted into the pump and removed from the pump 140 relatively easily.

Figure 25:
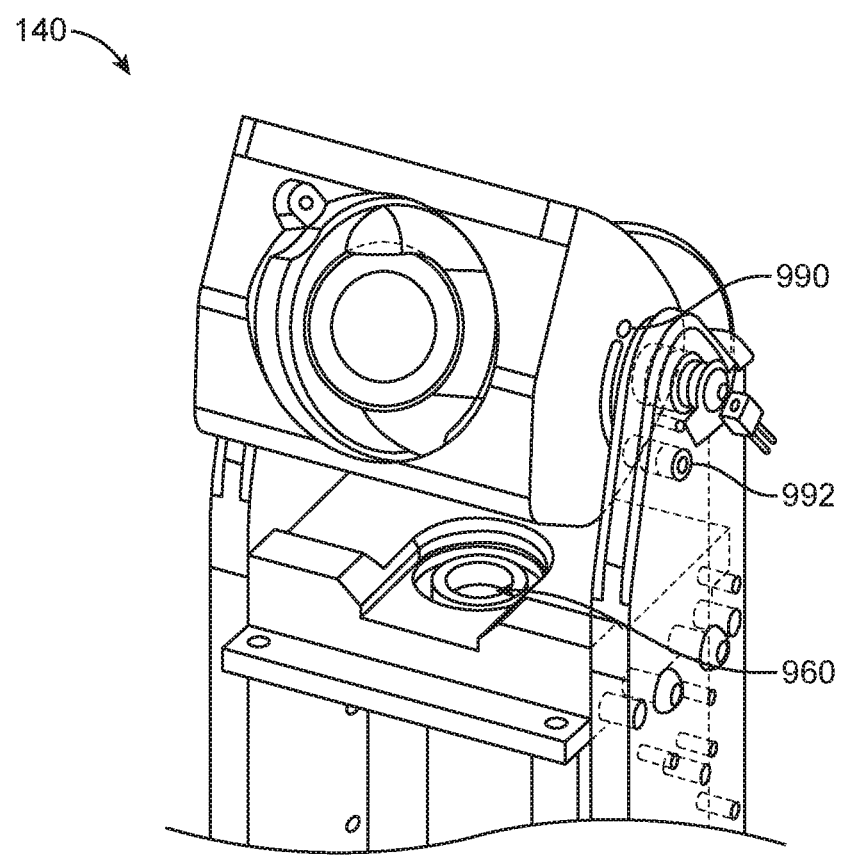
FIG. 25 is a perspective view of the syringe pump unit in accordance with an exemplary embodiment.

As shown in FIG. 24, the syringe pump unit 140 includes the syringe 900, the pressure jacket holder 970, sensor disks 920, a sensor 930, a pivot axis 940, a stop feature 950, a plunger 960 (FIG. 25), a pressure jacket holder 970, and a pressure jacket 980. The syringe 900 is supported in the pressure jacket 980, which is attached to a pressure jacket holder 970. The pressure jacket holder 970 is mounted to the syringe pump structure on pins 922 (FIG. 26), allowing the pressure jacket holder 970 to rotate as shown in FIG. 25 to allow loading and unloading of the syringe 900. In accordance with an exemplary embodiment, a ball spring plunger (not shown) and detents 990, 992 help the pressure jacket holder 970 stay in the positions needed for loading and operation.

As shown in FIG. 25, detent 990 is for a closed position, and detent 992 is for an open position. In addition, the sensor disks 920 can be mounted to the rotating pins 922, which allows the sensors on the syringe pump structure to detect a position of the pressure jacket holder 970 (FIG. 24) to prevent the plunger 960 (FIG. 26) from advancing before the pressure jacket holder 970 is in the operational position.

Figure 26:
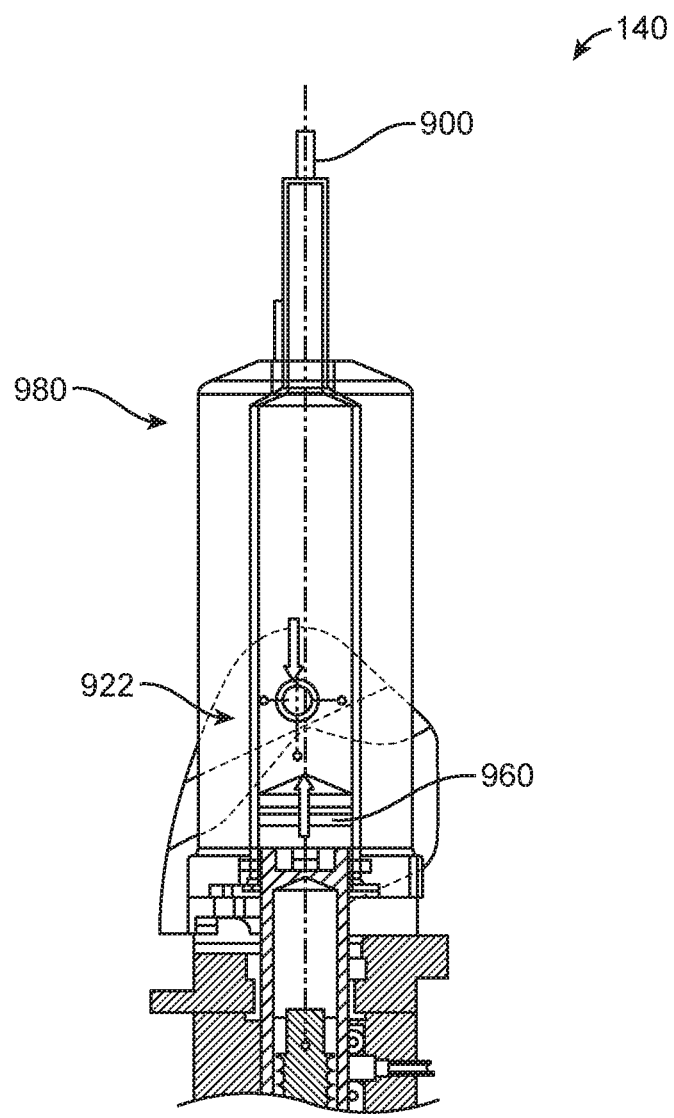
FIG. 26 is a perspective view of the syringe pump unit in accordance with an exemplary embodiment.

FIG. 26 is a perspective view of the syringe pump unit 140 in accordance with an exemplary embodiment. In accordance with an exemplary embodiment, a key feature in the design is the way the pressure jacket holder 970 reacts to the forces applied on it as shown in FIG. 26. In accordance with an exemplary embodiment, the pivot pins 922 can be offset from the axis of the syringe so that a moment is created when the syringe 900 is pressurized. The moment is an offset of the direction of the force applied by the pump plunger 960 and the direction of resistance to the force created by the rotational stop 950. The rotation caused by the pump plunger 960 is stopped by the rotational stop 950. In FIG. 26, the pressure jacket 980 would tend to rotate counterclockwise due to this moment. Stop features 950 (FIG. 24) on the pressure jacket 980 maintain the position when the moment is applied. With this arrangement, the pressure jacket holder 970 tends to close when the syringe 900 is pressurized, and no additional latching mechanism is needed to hold the pressure jacket 980 in place.

In accordance with an exemplary embodiment, the syringe 900 can include a liquid formulation. For example, the liquid formulation can include a lung surfactant or any other drug preparation adapted for delivery as an aerosol to an infant's lungs or a medicament to treat Respiratory Distress Syndrome (RDS) in infants or any other disease in children and adults. The liquid formulation can be contained within a dose container, such as, for example, a syringe 900, which can be pre-portioned.

The aerosol delivery system 100 is configured to supply the liquid formulation from the dose container at a constant and continuous rate to the heated capillary tube 650, wherein the liquid formulation is at least partially volatized. Alternatively, the liquid formulation is prepared by reconstituting a solid formulation (e.g., freeze-dried pharmaceutical formulation) with an appropriate pharmaceutically acceptable carrier such as, for example, water, buffer, or saline solution and optionally heated. Alternatively, multiple liquid formulations containing different drugs or reservoirs containing auxiliary substances other than drugs, for example, pharmaceutically acceptable carriers together with multiple feeding lines, can be provided as needed.

While various embodiments have been disclosed, it is to be understood that variations and modifications may be resorted to as will be apparent to those skilled in the art. Particularly, the outer shape of the transition adapter can be modified without affecting the inner structure. Such variations and modifications are to be considered within the purview and scope of the claims appended hereto.

What is claimed is:

1. A cartridge assembly, the cartridge assembly comprising:
- an active part of the cartridge assembly including a capillary tube;
- a susceptor, the susceptor configured to partially surround the capillary tube;
- a pair of displaceable covers, which surround at least the capillary tube and the susceptor;
- a handle and an insulator, wherein the handle is attached to the insulator and the insulator is arranged on an upper surface of the susceptor, the pair of displaceable covers at least partially surrounding the insulator and the susceptor, and
- wherein the pair of displaceable covers each includes heat dissipating fins, the heat dissipating fins configured to dissipate heat and create a space between a user and heated components of the cartridge assembly including a capillary tip of the capillary tube and the susceptor.

2. The cartridge assembly of claim 1, wherein the pair of displaceable covers each includes a protective arm, the protective arm configured to surround a distal end of the susceptor and a distal end of the capillary tube.

3. The cartridge assembly of claim 2, wherein the insulator includes at least one wicking path and at least one wicking port configured for applying a hardening agent and wherein the susceptor includes a first groove configured to contact the at least one wicking path and thereby creating a hollow structure adapted to receive the hardening agent such that upon hardening, the insulator and the susceptor are connected.

4. The cartridge assembly of claim 3, wherein the insulator includes one or more cut-outs adapted to dissipate the heat transfer from the susceptor to the handle.

5. The cartridge assembly of claim 3, wherein the susceptor has a second groove adapted to receive the capillary tube, wherein the distal end of the capillary tube and a proximal end of the capillary tube remain outside of the susceptor.

6. The cartridge assembly of claim 1, comprising:
a data card, the data card configured to identify the cartridge assembly and information related to the cartridge assembly.

7. The cartridge assembly of claim 1, wherein the cartridge assembly is disposable.

8. An aerosol delivery system, the aerosol delivery system comprising:
an aerosol delivery unit, the aerosol delivery unit comprising:
a cartridge receiver, which is configured to receive a cartridge assembly;
an inductor configured to receive the cartridge assembly and heat a liquid formulation within a capillary tube to produce an aerosol by induction heating; and
a pair of placement pins arranged within the cartridge receiver and configured to receive a cartridge assembly, the pair of placement pins configured to separate a pair of displaceable covers on the cartridge assembly from an active part of the cartridge assembly.

9. The aerosol delivery system of claim 8, comprising:
a pump, the pump comprising:
a container holder configured to receive a container containing the liquid formulation, and wherein the container holder is configured to pivot about an axis to expose an opening on a bottom of the container;
a plunger for applying a force to push the liquid formulation out of a distal end of the container into a proximal end of the capillary tube; and
a pressure jacket configured to support the container within the container holder.

10. The aerosol delivery system of claim 9, wherein the container is a syringe.

11. The aerosol delivery system of claim 9, comprising:
an operator's interface, the operator's interface having a display for inputting instructions for a delivery of the aerosol to a patient and/or treatment status of the patient; and
a power control unit, the power control unit configured to supply a source of power to at least one of the aerosol delivery unit, the pump, and the operator's interface.

12. The aerosol delivery system of claim 11, comprising:
a pole or wheel cart configured to receive one or more of the aerosol delivery unit, the syringe pump, the operator's interface, and the power control unit.

13. The aerosol delivery system of claim 8, further comprising:
a disposable aerosol tube set, which includes a transition adapter; and
a temperature probe, the temperature probe configured to monitor a temperature of the aerosol delivery unit to determine if the aerosol delivery unit is operating within the working temperature range of from approximately, 100° C. to 300° C.

14. The aerosol delivery system of claim 8, comprising:
the cartridge assembly configured to be placed within the cartridge receiver of
the aerosol delivery unit, the cartridge assembly including the pair of displaceable covers and the active part of the cartridge assembly, the active part of the cartridge assembly including a susceptor, a capillary tube at least partially surrounded by the susceptor, an insulator, and a handle, the insulator arranged between the susceptor and the handle and wherein the pair of displaceable covers is configured to surround the insulator, the capillary tube and the susceptor.

15. The aerosol delivery system of claim 14, wherein each of the displaceable covers includes heat dissipating fins, the heat dissipating fins configured to dissipate heat and create a space between a user and an exposed heated capillary tip and the susceptor.

16. The aerosol delivery system of claim 15, wherein each of the displaceable covers includes a protective arm, the protective arm configured to surround a distal end of the susceptor and a distal end of the capillary tube.

17. The aerosol delivery system of claim 8, comprising:
a cartridge identification assembly arranged within the cartridge receiver, the cartridge identification assembly configured to identify a data card on the cartridge assembly.

18. The aerosol delivery system of claim 8, wherein the aerosol delivery unit includes a cartridge lock, the cartridge lock configured to lock the cartridge assembly within the cartridge receiver.

19. The aerosol delivery system of claim 8, wherein the inductor includes an induction coil, which is configured to heat a susceptor, and wherein the induction coil comprises a wire wound around one or more graphite cores.

20. The aerosol delivery system of claim 8, comprising:
a transition adapter for receiving the aerosol and combining the aerosol with a carrier gas, wherein the transition adapter includes a transition adapter flag adapted to be detected by a sensor when the transition adapter is being placed within the cartridge receiver.

21. The aerosol delivery system of claim 20, wherein the transition adapter comprises:
a housing having a proximal end and a distal end, the proximal end having an aerosol passage for receiving the aerosol from the capillary tube and the distal end having an exit port, the housing having a length between the distal end and the proximal end;
a carrier gas connection port for receiving the carrier gas from a gas source, which is in communication with a plurality of carrier gas exit ports, the plurality of carrier gas exit ports are arranged adjacent to the aerosol passage in a pattern that partially encircles the flow of aerosol;
an inner cavity, which is adapted to receive the aerosol from the aerosol passage and the carrier gas from the plurality of carrier gas exit ports and to direct streams of carrier gas to at least partially encircle and flow in parallel with a main direction of a flow of the aerosol along the length of the housing toward the exit port; and
the exit port on the distal end of the housing configured for delivery of aerosol to a patient in need of an aerosolized active agent.

22. The aerosol delivery system of claim 21, wherein the inner cavity has a proximal portion having a conical inner wall, which expands outward towards the distal end of the housing, and a distal portion having a tapered inner diameter; and
wherein the carrier gas connection port for receiving the carrier gas from the gas source includes at least one gas entry port for receiving the carrier gas, the at least one gas entry port directing a stream of carrier gas to one or more gas exit ports.

23. The aerosol delivery system of claim 20, wherein the cartridge receiver includes:
an active alignment groove configured to guide the active part of the cartridge assembly into the inductor, a transition adapter cavity, and a transition adapter placement groove, which connects with the transition adapter flag on the trans the transition adapter is inserted into the transition adapter placement groove, the transition adapter flag is detected by the sensor, which signals that the transition adapter has been placed in the cartridge receiver.

24. The aerosol delivery system of claim 8, wherein the aerosol delivery unit includes a plurality of sensors, the plurality of sensors configured to detect a presence of the cartridge assembly and/or the active part of the cartridge assembly within the cartridge receiver, a presence of a transition adapter within the cartridge receiver, and an engagement of a capillary tip of the capillary tube with the transition adapter within the cartridge receiver of the aerosol delivery unit upon moving the active part of the cartridge assembly from a proximal end of the cartridge receiver to a distal end of the cartridge receiver.

25. A method of producing an aerosol, the method comprising:
  placing a cartridge assembly into a cartridge receiver of an aerosol delivery unit, the cartridge assembly including (a) an active part of the cartridge assembly comprising (i) a capillary tube, (ii) a susceptor configured to at least partially surround the capillary tube, (iii) a handle, and (iv) an insulator, the handle and the insulator arranged on an upper surface of the susceptor, and (b) a pair of displaceable covers, which at least partially surround the insulator, the capillary tube, and the susceptor, each of the displaceable covers including a protective arm, the protective arm configured to surround a distal end of the susceptor and a distal end of the capillary tube; and
  displacing the pair of displaceable covers by moving the active part of the cartridge assembly into an inductor.

26. The method of claim 25, comprising:
heating a liquid formulation within the capillary tube into an aerosol by induction with the inductor.

27. The method of claim 26, comprising:
  supplying the liquid formulation from a syringe pump, the syringe pump including a syringe holder configured to receive a syringe containing the liquid formulation, and wherein the syringe holder is configured to pivot about an axis to expose an opening on a bottom of the syringe;
  applying a force to a plunger to push the liquid formulation out of a distal end of the syringe into a proximal end of the capillary tube housed in the aerosol delivery unit; and
  supporting the syringe within the syringe holder with a pressure jacket.

28. The method of claim 25, wherein the aerosol delivery unit includes a plurality of sensors, the method further comprising:
  detecting a presence of the cartridge assembly and/or the active part of the cartridge assembly within the cartridge receiver;
  detecting a presence of a transition adapter within the cartridge receiver with; and/or
  detecting an engagement of a capillary tip of the capillary tube and the transition adapter within the cartridge receiver.

29. The method of claim 25, comprising:
monitoring a temperature of the aerosol delivery unit with a temperature sensor to determine if the aerosol delivery unit is operating within the working temperature range of from approximately, 150° C. to 300° C.

30. The method of claim 25, comprising:
separating the displaceable covers on the cartridge assembly from the active part of the cartridge assembly upon moving the active part of the cartridge assembly from a position in which the cartridge assembly is placed into the cartridge receiver.

31. The method of claim 25, comprising:
identifying a data card on the cartridge assembly with a cartridge identifier assembly arranged within the cartridge receiver.

32. The method of claim 25, comprising:
locking the active part of the cartridge assembly within the cartridge receiver during heating of the capillary tube and susceptor.

33. The method of claim 25, wherein each of the displaceable covers includes heat dissipating fins, the heat dissipating fins configured to dissipate heat and create a space between a user and heated parts of the active part of the cartridge assembly.

34. The method of claim 26, comprising:
combining the aerosol with a carrier gas in an aerosol transition adapter.

* * * * *